US007767437B2

(12) United States Patent
Gau

(10) Patent No.: US 7,767,437 B2
(45) Date of Patent: Aug. 3, 2010

(54) SYSTEM FOR DETECTION OF A COMPONENT IN A LIQUID

(75) Inventor: Vincent Jen-Jr Gau, Los Angeles, CA (US)

(73) Assignee: GeneFluidics, Inc., Monterey Park, CA (US)

( * ) Notice: Subject to any disclaimer, the term of this patent is extended or adjusted under 35 U.S.C. 154(b) by 0 days.

(21) Appl. No.: 10/288,320

(22) Filed: Nov. 4, 2002

(65) Prior Publication Data

US 2003/0148342 A1 Aug. 7, 2003

Related U.S. Application Data

(60) Provisional application No. 60/339,766, filed on Nov. 2, 2001, provisional application No. 60/399,058, filed on Jul. 26, 2002.

(51) Int. Cl.
*C12M 1/38* (2006.01)

(52) U.S. Cl. ................. 435/287.2; 435/287.3; 435/149; 436/518; 422/50; 422/68.1; 422/82.01

(58) Field of Classification Search .................. 436/94, 436/102, 178; 422/100, 102; 204/600, 601; 205/775; 435/287.2
See application file for complete search history.

(56) References Cited

U.S. PATENT DOCUMENTS

| | | | | |
|---|---|---|---|---|
| 4,323,536 | A | 4/1982 | Columbus | |
| 4,399,225 | A * | 8/1983 | Hansen et al. | 436/34 |
| 4,426,451 | A | 1/1984 | Columbus | |
| 5,296,123 | A * | 3/1994 | Reddy et al. | 205/775 |
| 5,571,410 | A * | 11/1996 | Swedberg et al. | 210/198.2 |
| 5,932,799 | A * | 8/1999 | Moles | 73/53.01 |
| 5,972,199 | A * | 10/1999 | Heller et al. | 205/777.5 |
| 6,030,581 | A * | 2/2000 | Virtanen | 422/68.1 |
| 6,117,290 | A | 9/2000 | Say | |
| 6,128,820 | A * | 10/2000 | Nolan et al. | 29/889.1 |
| 6,167,910 | B1 * | 1/2001 | Chow | 137/827 |
| 6,251,343 | B1 * | 6/2001 | Dubrow et al. | 422/102 |
| 6,331,439 | B1 | 12/2001 | Cherukuri | |
| 6,440,725 | B1 * | 8/2002 | Pourahmadi et al. | 435/288.5 |
| 6,454,924 | B2 * | 9/2002 | Jedrzejewski et al. | 204/601 |
| 6,498,353 | B2 * | 12/2002 | Nagle et al. | 250/573 |
| 6,572,830 | B1 * | 6/2003 | Burdon et al. | 422/186.29 |
| 6,582,963 | B1 * | 6/2003 | Weigl et al. | 436/52 |
| 6,632,619 | B1 * | 10/2003 | Harrison et al. | 435/7.2 |
| 6,670,115 | B1 * | 12/2003 | Zhang | 435/5 |
| 2001/0026778 | A1 * | 10/2001 | Ackley et al. | 422/129 |
| 2001/0045357 | A1 * | 11/2001 | Broadley et al. | 204/435 |
| 2002/0012616 | A1 * | 1/2002 | Zhou et al. | 422/130 |

(Continued)

OTHER PUBLICATIONS

Polysiloxanes, Encyclopedia Britannica.*

(Continued)

*Primary Examiner*—N. C. Yang
(74) *Attorney, Agent, or Firm*—Gavgilovich, Dodd & Lindsey, LLP

(57) ABSTRACT

The system includes a liquid transport structure configured to hold a sensor for detecting one or more components in a liquid. The liquid transport structure includes a reservoir configured to hold a liquid within the liquid transport structure and a channel configured to transport a liquid held in the reservoir to a sensor held by the liquid transport structure.

29 Claims, 19 Drawing Sheets

U.S. PATENT DOCUMENTS

2002/0177135 A1* 11/2002 Doung et al. .................. 435/6
2005/0244954 A1* 11/2005 Blackburn et al. ....... 435/287.2

OTHER PUBLICATIONS

Gau, et al., "Enzyme-Based Electrochemical Biosensor with DNA Array Chip," Jun. 2000, 1-56.

Gau, Jen-Jr, "Enzyme-Based Electrochemical DNA Detector Chip Using MEMS Technology," Mar. 2001, 1-56.

"A MEMS Based Amperometric Detector for *E. coli* Bacteria Using Self-Assembled Monolayers," Jun. 2001, 1-18.

* cited by examiner

SYSTEM FOR DETECTION OF A COMPONENT IN A LIQUID

RELATED APPLICATIONS

This application claims priority to provisional patent application Ser. No. 60/339,766 filed on Nov. 2, 2001, entitled "Integrated Sample Preparation Unit" and incorporated herein in its entirety. This application is related to patent application Ser. No. 60/399,058 filed on Jul. 26, 2002, entitled "Assay System Employing a Cartridge" and incorporated herein in its entirety.

BACKGROUND

1. Field of the Invention

The invention relates to assay equipment. More particularly, the invention relates to a system having a liquid transport structure for use with assay equipment.

2. Background of the Invention

A variety of assays have been developed for detecting the presence of one or more target agents in a liquid. This liquid is often prepared from a sample that is believed to have the target agent. The sample must often be transported from a site where the sample is obtained to a laboratory where the assay is performed. An undesirable amount of time is often associated with transporting the sample to the laboratory. As a result, there is a need for an assay system that can be performed in the field.

SUMMARY OF THE INVENTION

The invention relates to an apparatus for use with assay equipment. The apparatus includes a liquid transport structure having a reservoir configured to hold a liquid within the liquid transport structure. The apparatus includes an outlet channel configured to transport a liquid held in the reservoir to a chamber within the liquid transport structure.

Another embodiment of the apparatus includes a liquid transport structure configured to hold a sensor for detecting one or more components in a liquid. The liquid transport structure includes a reservoir configured to hold a liquid within the liquid transport structure and a channel configured to transport a liquid held in the reservoir to a sensor held by the liquid transport structure. The liquid transport structure can also include an inlet channel extending from an external side of the liquid transport structure to the reservoir.

In some instances, the liquid transport structure includes a first member positioned over the sensor and a second member positioned under the sensor. The first member and/or the second member can include a base and a cover. The base and the cover can each define a portion of the reservoir.

The liquid transport structure can be removably coupled with an interface system that provides liquid communication between the reservoir and one or more tubes. In some instances, the liquid transport structure is configured to be clamped between two or more members of the interface system.

The liquid transport structure can hold a sensor structure that includes the sensor positioned on a sensor support. In some instances, the sensor structure is configured to be removed from the liquid transport structure. The sensor structure can include a plurality of sensors positioned on the sensor support. Further, the liquid transport structure can define a plurality of reservoirs that are each configured to hold a liquid within the liquid transport structure. The liquid transport structure can also include a plurality of channels that are each configured to transport a liquid from a reservoir to a sensor on the sensor structure.

The sensor can include a plurality of electrodes positioned on the sensor support. The electrodes can include a reference electrode and a counter electrode that are each spaced apart from a working electrode.

The invention also relates to a sensor having an electrode support with a first support region spaced apart from a second support region. One or more electrodes are positioned on the first support region and one or more of the electrodes positioned on the second support region. In some instances, a working electrode is positioned on the second support region, a reference electrode is positioned on the first support region and a counter electrode is positioned on the first support region.

The invention also relates to a method for performing an assay. The method includes changing the pressure on a liquid stored in a reservoir of a liquid transport structure. The pressure is changed such that at least a portion of the liquid flows from the reservoir onto a sensor held by the liquid transport structure. The pressure can be changed by increasing pressure in an inlet channel extending from an external side of the liquid transport structure to the reservoir and/or by reducing pressure in an outlet channel extending from the reservoir to a chamber formed over the sensor.

Another embodiment of the method includes applying one or more liquids to a sensor such that a target agent bonds to the sensor along with one or more non-target agents. The sensor is configured to detect a component in a liquid and includes two or more electrodes positioned on a sensor support. The method also includes removing non-target agents from the sensor. Removing the non-target agents can include flowing a liquid across the sensor. The liquid can be flowed across the sensor so as to generate a shear flow pattern on the sensor. In some instances, a liquid transport structure defines a chamber over the sensor and flowing the liquid across the sensor includes flowing the liquid through the chamber.

DETAILED DESCRIPTION OF THE PREFERRED EMBODIMENT

The invention relates to a liquid transport structure for use with an assay. The liquid transport structure holds one or more sensors for the detection of a component in a liquid. A suitable sensor is an electrochemical sensor including a plurality of electrodes formed on a sensor support. These sensors can have a compact size that is suitable for use with small volumes of liquid.

The liquid transport structure can include inlet channels that each extend from an outside surface of the liquid transport structure to a reservoir located inside of the holder. The liquid transport structure can also include a plurality of outlet channels that are each configured to carry a liquid from a reservoir to a sensor held within the liquid transport structure. Liquids that are to be employed during an assay can be stored in each of the reservoirs or delivered into the reservoirs from an outside source. Each liquid can be transported onto the sensor at the desired time. The ability to store these solutions in the reservoir allows the liquid transport structure to be used in the field.

The liquid transport structure can be interfaced with assay equipment such as pumps, vacuums and valves for controlling the flow of liquid from the reservoirs. The liquid transport structure can be constructed so as to be easily coupled with the assay equipment and easily removed from the assay equipment. As a result, different liquid transport structures can be used with the assay equipment. Accordingly, the liquid transport system provides a wide range of flexibility.

Figure 1A:
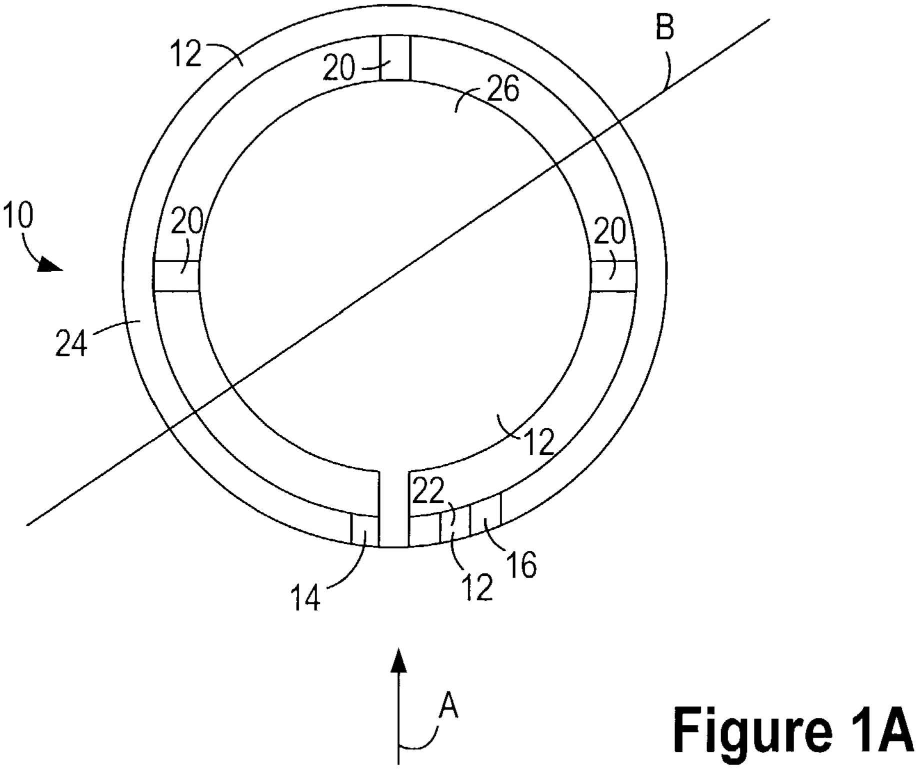
FIG. 1A is a topview of a sensor configured to detect a component in a liquid.
Figure 1B:
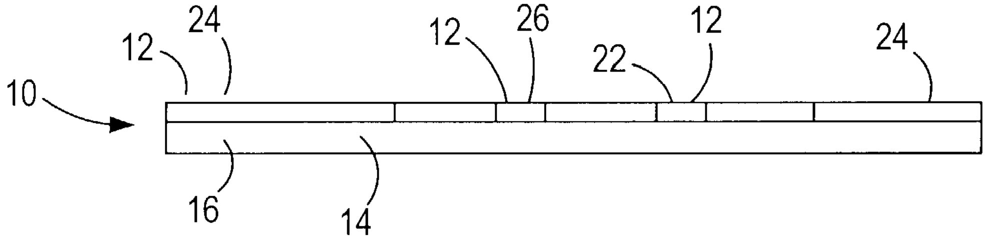
FIG. 1B is a sideview of the sensor taken in the direction of the arrow labeled A in FIG. 1A.
Figure 1C:
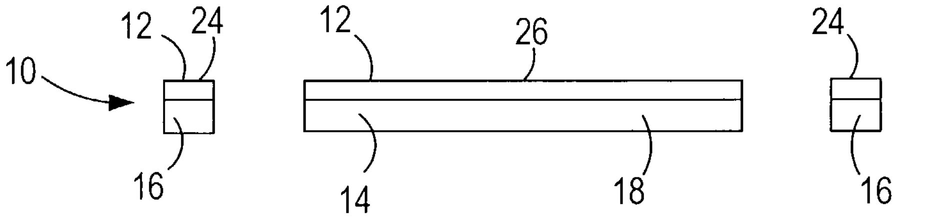
FIG. 1C is a cross section of the sensor taken at the line labeled B in FIG. 1A.

FIG. 1A through FIG. 1C illustrate an example of a sensor 10 configured to detect a component in a liquid. FIG. 1A is a topview of the sensor 10 and FIG. 1B is a sideview of the sensor 10 shown in FIG. 1A taken in the direction of the arrow labeled A. FIG. 1C is a cross section of the sensor 10 shown in FIG. 1A taken at the line labeled B.

The sensor 10 includes a plurality of electrodes 12 positioned on an electrode support 14. The electrode support 14 includes a first support region 16 spaced apart from a second support region 18. One or more tether members 20 immobilize the position of the first support region 16 relative to the second support region 18. Although the first support region 16 is shown as surrounding the second support region 18, the first support region 16 need not surround the entire second support region 18.

A reference electrode 22 and a counter electrode 24 are spaced apart from one another on the first support region 16. A working electrode 26 is formed on the second support region 18. A portion of the working electrode 26 extends from the second support region 18 across a tether member 20 to the first support region 16. As will be illustrated below, the portion of the working electrode 26 positioned on the first support region 16 can serve as a contact pad.

The sensor 10 can be constructed such that the largest dimension of the working electrode 26 is less than 1 μm, 10 μm, 50 μm, 100 μm, 1 mm or 10 mm. Suitable widths for the counter electrode 24 and the reference electrode 22 include, but are not limited to, widths less than 1 μm, 10 μm, 100 μm, 500 μm, 0.1 mm, 1 mm or 5 mm. Suitable dimensions for the gap between the working electrode 26 and the reference electrode 22 and/or between the working electrode 26 and the counter electrode 24 include, but are not limited to, gaps less than 0.1 μm, 10 μm, 50 μm, 200 μm, 0.5 mm or 2 mm. These dimensions can provide for a sensor 10 having a compact size that is suitable for use in on site assay equipment.

Suitable materials for the sensor 10 support include, but are not limited to, plastics, polymers, glass, silicon substrates and metals. Suitable material for the working electrode 26 include, but are not limited to, gold, silver, copper, platinum, chromium, aluminum, titanium, nickel and conducting polymers. Suitable methods for forming the electrodes 12 on the electrode support 14 include, but are not limited to, lift-off processes with photolithography, thin film deposition with shadow mask and thin film foil pressing.

Figure 1D:
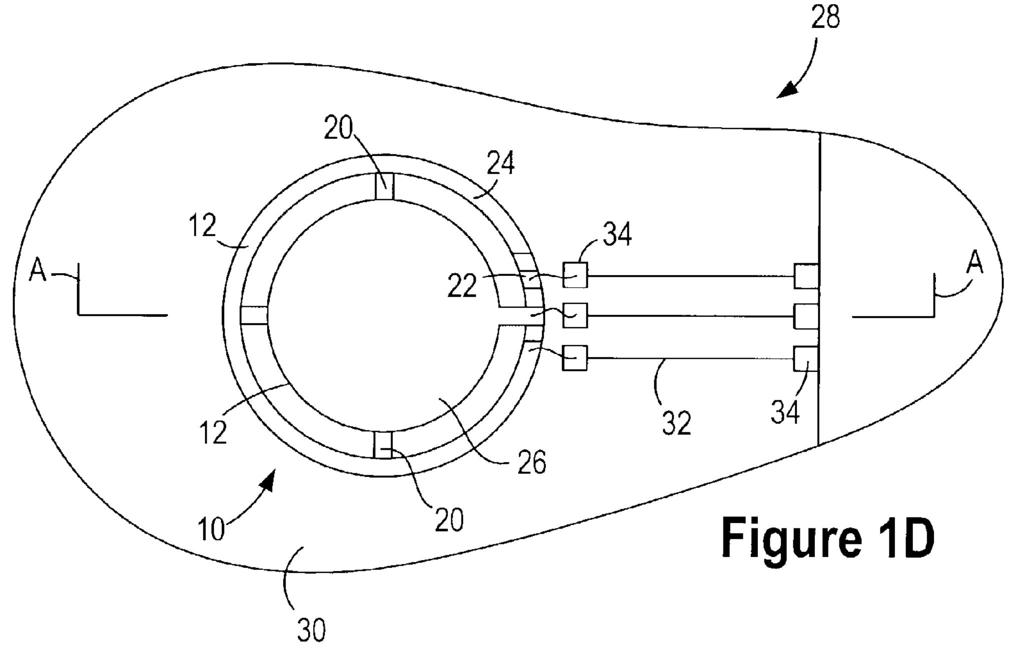
FIG. 1D illustrate a sensor structure having the sensor illustrated in FIG. 1A through FIG. 1C bonded to a sensor support.
Figure 1E:
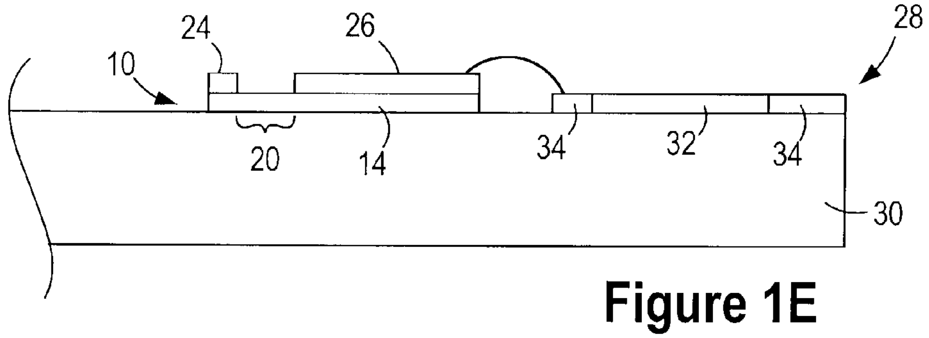
FIG. 1E is a cross section of the sensor structure taken along a line extending between the brackets labeled A in FIG. 1D.

FIG. 1D and FIG. 1E illustrate a sensor 10 structure employing the sensor 10 illustrated in FIG. 1A through FIG. 1C. FIG. 1D is a topview of the sensor 10 structure. FIG. 1E is a cross section of the sensor structure 28 taken along a line extending between the brackets labeled A in FIG. 1D.

The sensor structure 28 includes the sensor 10 illustrated in FIG. 1A through FIG. 1C bonded to a sensor support 30. Suitable materials for the sensor support 30 include, but are not limited to, plastics, polymers, glass, silicon and metals. A suitable method for bonding the sensor 10 to the sensor support 30 includes, but is not limited to, gluing, ultrasonic bonding, taping, welding and pressing. Electrical conductors 32 provide electrical communication between pads 34 positioned at a side of the sensor structure 28 and pads positioned adjacent to the sensor 10. The pads adjacent to the sensor 10 are in electrical communication with the electrodes. For instance, the pads adjacent to the sensor 10 can be wire bonded to the electrodes 12. The pads 34 at the side of the sensor structure can be connected to a coupler (not shown) to provide electrical communication between the electrodes 12 and electronics for operating the sensor 10. Alternatively, the pads 34 can be directly coupled with wires that provide electrical communication between the sensor 10 and the electronics. Suitable conductors 32 include, but are not limited to, metal traces formed on the sensor support 30 using integrated circuit manufacturing techniques or printed circuitry techniques.

Figure 2A:
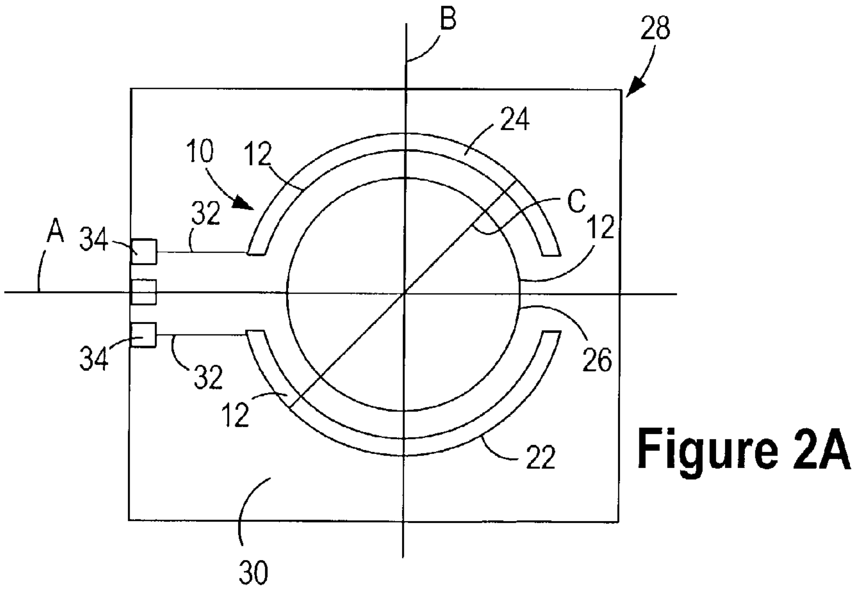
FIG. 2A is a topview of another embodiment of a sensor structure.
Figure 2B:
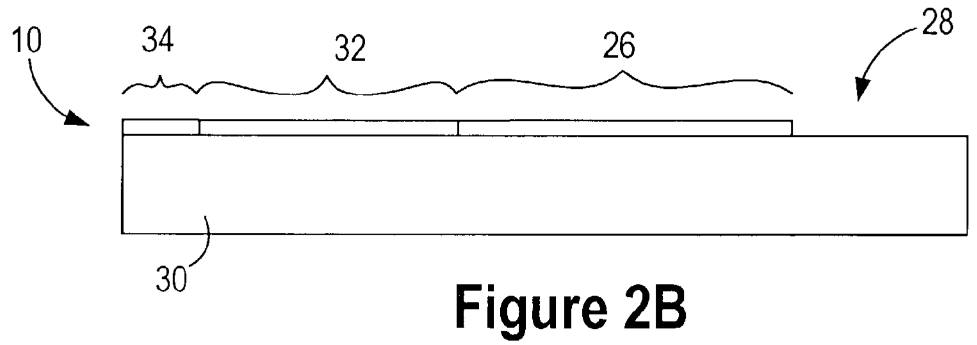
FIG. 2B is a cross section of the sensor structure taken along the line labeled A in FIG. 2A.
Figure 2C:
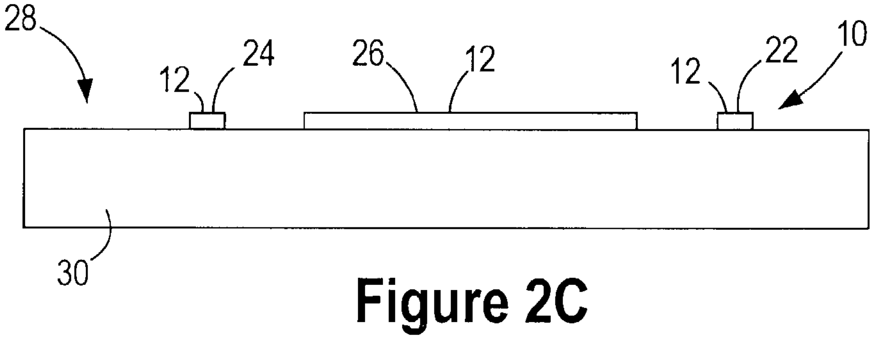
FIG. 2C is a cross section of the sensor structure taken along the line labeled B in FIG. 2A.

FIG. 2A through FIG. 2C illustrate another embodiment of a sensor structure 28. FIG. 2A is a topview of the sensor structure 28 and FIG. 2B is a cross section of the sensor structure 28 shown in FIG. 2A taken along the line labeled A. FIG. 2C is a cross section of the sensor structure 28 shown in FIG. 2A taken along the line labeled B.

The electrodes 12 of a sensor 10 are formed directly on the sensor support 30. Accordingly, the sensor support 30 serves as the electrode support 14 disclosed with respect to FIG. 1A through FIG. 1C. Electrical conductors 32 provide electrical communication between each of the electrodes 12 and a pad 34. The electrodes 12, the conductors 32 and the pads 34 can be formed on the sensors 10 support using the thin film deposition and photo-lithography techniques employed in integrated circuit manufacturing.

Figure 3:
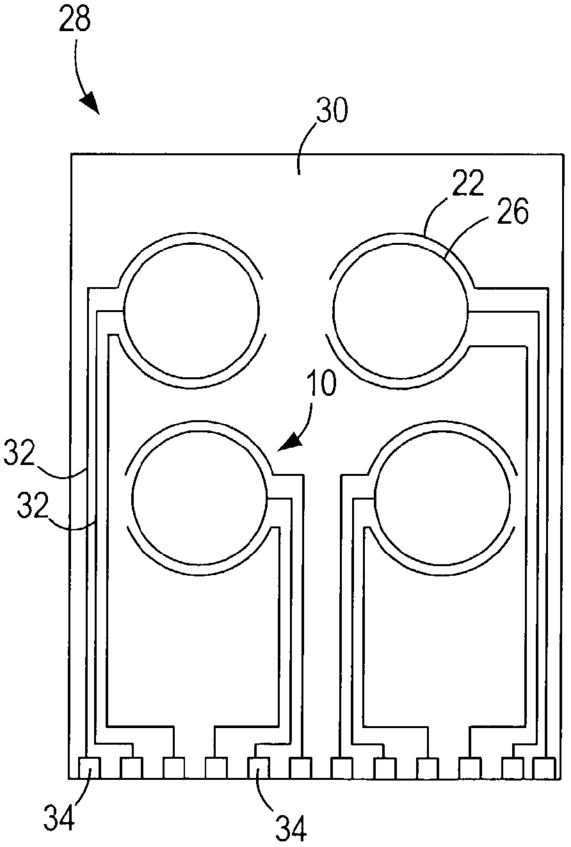
FIG. 3 is a topview of a sensor structure having a plurality of sensors on a sensor support.

Although FIG. 1A through FIG. 2C illustrate the sensor structure 28 as having a single sensor 10, a sensor structure 28 can include a plurality of sensors 10 as illustrated in FIG. 3. The sensors 10 can be arranged in an array on the sensor structure 28. Each of the sensors 10 includes a working electrode 26, a reference electrode 22 and a counter electrode 24. Electrical conductors 32 provide electrical communication between each of the electrodes 12 and a pad 34 positioned at a side of the sensor structure 28. Although each of the pads 34 is shown as being positioned along the same side of the sensor structure 28, the pads 34 can be positioned on different sides of the sensor structure 28.

Figure 4:
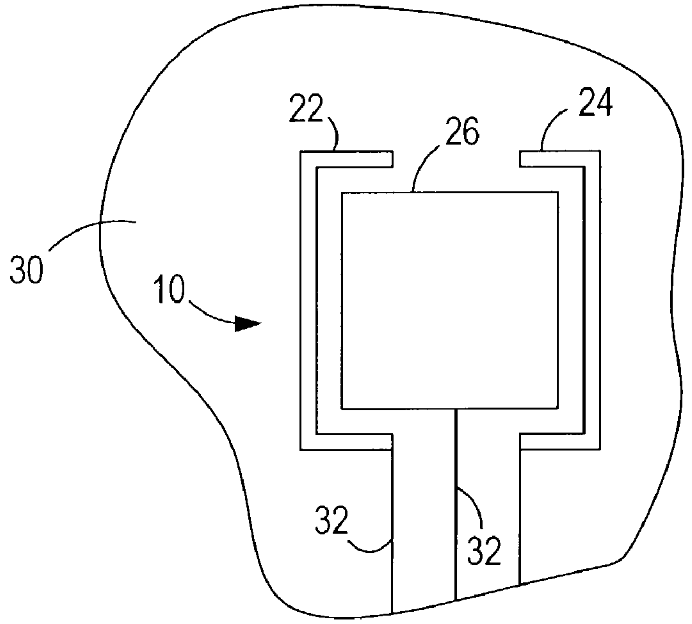
FIG. 4 is a topview of a sensor having a rectangular perimeter.

Although the working electrode 26 is shown above as having a round shape, the working electrode 26 can have a variety of other shapes including, but not limited to, rectangular shapes, triangular shapes and wedge shapes as illustrated in FIG. 4.

Figure 5A:
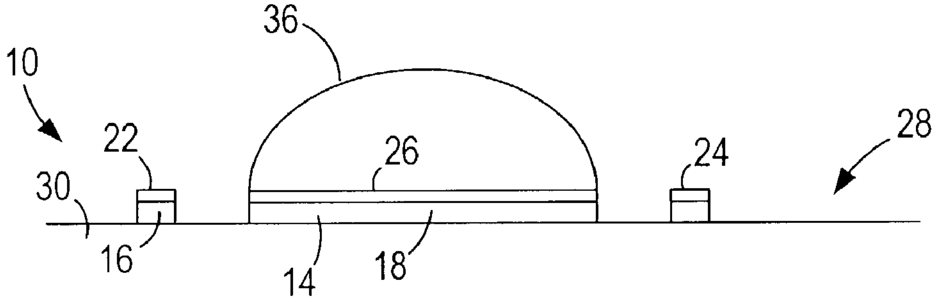
FIG. 5A illustrates a drop of a liquid formed constrained over the working electrode of a sensor.
Figure 5B:
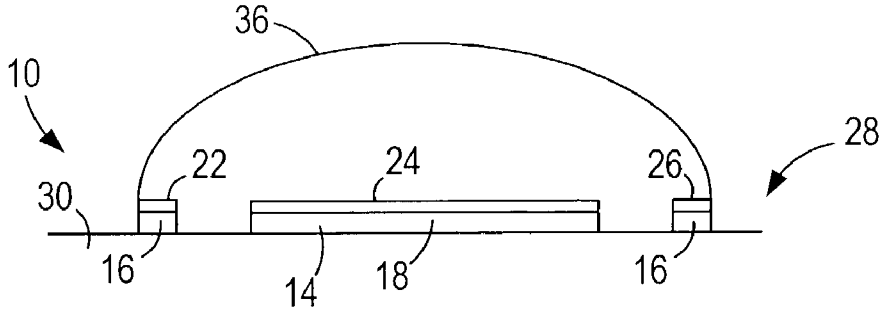
FIG. 5B illustrates a drop of a liquid formed constrained over the working electrode, the reference electrode and the counter electrode of a sensor.

During operation of a sensor 10, one or more liquids are transported onto the sensor 10. In some instances, a liquid positioned on the sensor structure 28 is washed off the sensor structure 28 and replaced with a different liquid. A liquid transported onto the sensor structure 28 can be confined to the working electrode 26 in the shape of a drop 36 as shown in FIG. 5A or can be formed over each of the electrodes 12 as shown in FIG. 5B.

The sensors 10 described above can be operated as electrochemical sensors 10. For instance, the one or more liquids transported onto a sensor 10 are selected so as to bond a target agent to the sensor 10 and/or to the sensor support 30. Examples of target agents include, but are not limited to, DNA strands, proteins, small molecules and cells. A target DNA strand can be bonded to the sensor 10 by bonding a DNA strands with a complementary region to the sensor 10 and then transporting onto the sensor 10 a liquid containing the target DNA strand. Further, bonding to the sensor 10 antibodies that specifically bind to the target cell and then transporting onto the sensor 10 a liquid containing the target cell can serve to bond a target cell to the sensor 10. As noted above, one or more liquids are transported onto the sensor 10 so as to bond the target agent to the sensor 10 and/or to the sensor support 30. Examples of methods for bonding various components to the sensor 10 and/or the sensor support 30 are described in U.S. patent application Ser. No. 09/848,727, filed on May 3, 2001, entitled "Biological Identification System with Integrated Sensor Chip" and incorporated herein in its entirety.

Once the target agent has been bonded to the sensor 10, a sample to be tested for the presence of the target agent is prepared by transporting onto the sensor 10 a liquid contains one or more first components that interact with the target agent so as to produce a second component in the sample. In some cases, the target agent can be modified by a signal agent to react with the first component. The sample is tested by applying a potential between the working electrode 26 and the reference electrode 22 while monitoring current passing through a circuit that includes the working electrode 26, the sample and the counter electrode 24. The potential applied between the working electrode 26 and the reference electrode 22 is raised to a level sufficient to cause electron transfer between the working electrode 26 and second component that diffuses from the target agent to the working electrode 26. In some case, the electron transfer between the target agent and the working electrode 26 can be monitored. The electron transfer allows current to flow through the circuit. A current flowing through the working electrode 26 and the counter electrode 24 indicates that the target agent is present in the sample while the lack of current indicates that the component is not present in the sample. Because the first component interacts with the target agent to produce the second component in the sample, the presence of the second component in the liquid indicates the presence of the target agent. In some instances, the direct electron transfer between the target agent and the working electrode 26 is monitored instead of monitoring the secondary components.

Because the sensors 10 illustrated above can be operated as electrochemical sensors 10, coulometric, amperometric and/or voltametric methods can be employed to quantify the concentration of the target agent in the sample.

The sensor 10 described above can be operated using other methods. For instance, the target agent can also be the component that diffuses to the sensor 10 and transfers electrons with the working electrode 26.

A variety of mechanisms are available for constraining a liquid to the working electrode 26 or over each of the electrodes 12. For instance, when the surface of working electrode 26 is elevated relative to the sensor support 30 as shown in FIG. 5A, the surface tension of the liquid can serve to confine the drop 36 to the working electrode 26. Further, when the surface of the counter electrode 24 and the surface of the reference electrode 22 are elevated relative to the sensor support 30 as shown in FIG. 5B, the surface tension of the liquid can serve to confine the drop 36 within the perimeter of the reference electrode 22 and the counter electrode 24. In some cases, the surface of working electrode 26 is suspended over the sensor support 30 or isolated to employ surface tensions to confine the liquid on the surface of the working electrode 26.

Elevating one or more electrodes 12 relative to a sensor support 30 can be achieved by selecting an electrode support 14 with the desired thickness. Alternatively, a trench can be etched between the working electrode 26 and the reference electrode 22, between the working electrode and the counter electrode 24, around the outside of the reference electrode 22 and/or around the outside of the counter electrode 24. When the sensor structure 28 is constructed as shown in FIG. 2A through FIG. 2C, the electrodes 12 can be formed with sufficient thickness to elevate the drop relative to the sensor support 30 and/or a recess can be formed in the sensor support 30 adjacent to the electrode 12. When a surface of an electrode 12 is to be elevated so as to constrain a liquid to the electrode 12, a suitable height for the surface of an electrode 12 includes, but is not limited to, heights greater than 0.5 μm, 10 μm, 500 μm and 5 mm.

Other mechanisms are available for constraining a liquid to a sensor 10. For instance, all or a portion of the upper surface of the sensor support 30 can be hydrophobic. In some instances, the portion of the upper surface between the reference electrode 22 and the working electrode 26 and between the counter electrode 24 and the working electrode 26 is hydrophobic. An aqueous liquid transported onto the working electrode 26 will remain constrained on the working electrode 26 until enough liquid is transported onto the working electrode 26 to overcome the hydrophobic nature of the upper surface and cross over the gap between the working electrode 26 and the reference electrode 22 and/or the gap between the working electrode and the counter electrode 24. Accordingly, the hydrophobic nature of the upper surface can serve to constrain a drop of the liquid to the working electrode 26.

When the portion of the upper surface located outside of the counter electrode 24 and the reference electrode 22 is also hydrophobic, an aqueous liquid transported onto the sensor structure 28 is driven onto the reference electrode 22, the counter electrode 24 and the working electrode 26. Accordingly, the hydrophobic nature of the upper surface can serve to constrain a drop of the liquid to the reference electrode 22 and the counter electrode 24.

A variety of techniques can be employed to create a hydrophobic sensor support 30. For instance, the sensor support 30 can be constructed of a hydrophobic medium such as most plastics and polymers. Alternatively, the sensor support 30 can be constructed of a medium having a hydrophobic coating or treatment. Glass and silicon are examples of media that are suitable for use with hydrophobic coating.

In some instances, the exposed surfaces of the working electrode 26, the reference electrode 22 and/or the counter electrode 24 are hydrophilic. The hydrophilic nature of the electrodes 12 serves to draw the liquid onto the electrodes 12.

Accordingly, the hydrophilic nature of the electrodes 12 can serve to constrain liquid to the working electrode 26, the reference electrode 22 and/or the counter electrode 24.

A variety of techniques can be employed to create one or more hydrophilic electrodes 12. For instance, an electrode 12 can be coated with a hydrophilic medium. As an example, a working electrode 26 constructed of gold can have a protein coating.

Figure 6:
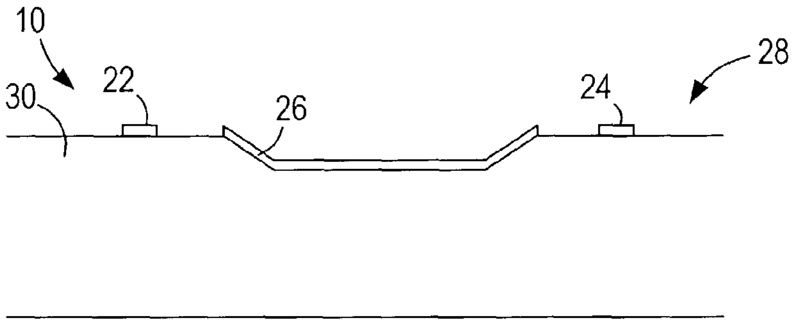
FIG. 6 illustrates a sensor structure having a sensor formed on a sensor support. The sensor support includes a well shaped so as to constrain a liquid over the sensor.

The sensor support 30 can include a well as shown in FIG. 6. The well can serve to constrain the liquid to a particular region of the sensor structure 28. The working electrode 26 can cover the bottom and sides of the well or only a portion of the well. Alternatively, the working electrode 26 can extend from inside the well to outside the well. In some instances, the reference electrode 22 and the counter electrode 24 are also positioned in the well.

Figure 7A:
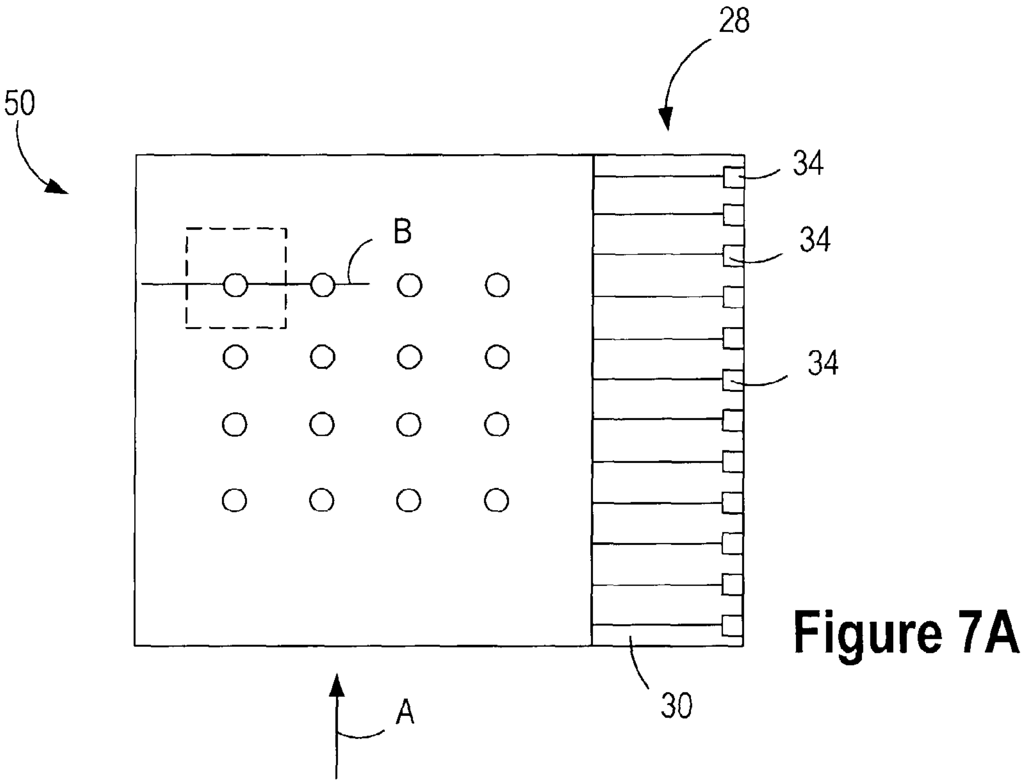
FIG. 7A is a topview of a liquid transport system configured to hold a sensor structure. The liquid transport system includes a reservoir and is configured to transport a liquid from the reservoir to a sensor included on the sensor structure.
Figure 7B:
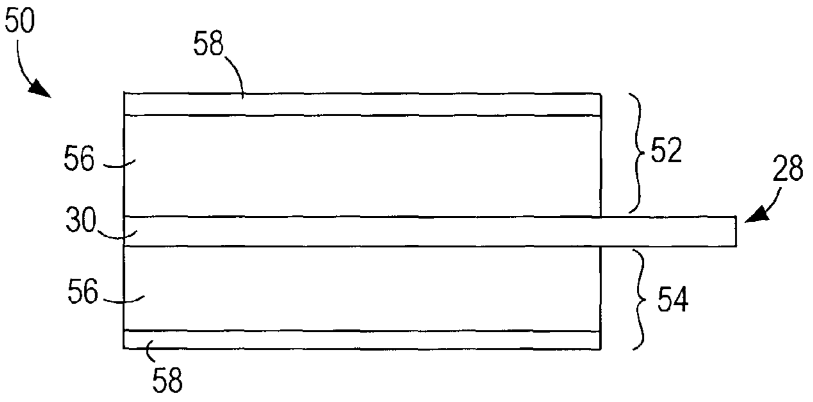
FIG. 7B is a sideview of the liquid transport structure taken in the direction of the arrow labeled A in FIG. 7A.
Figure 7C:
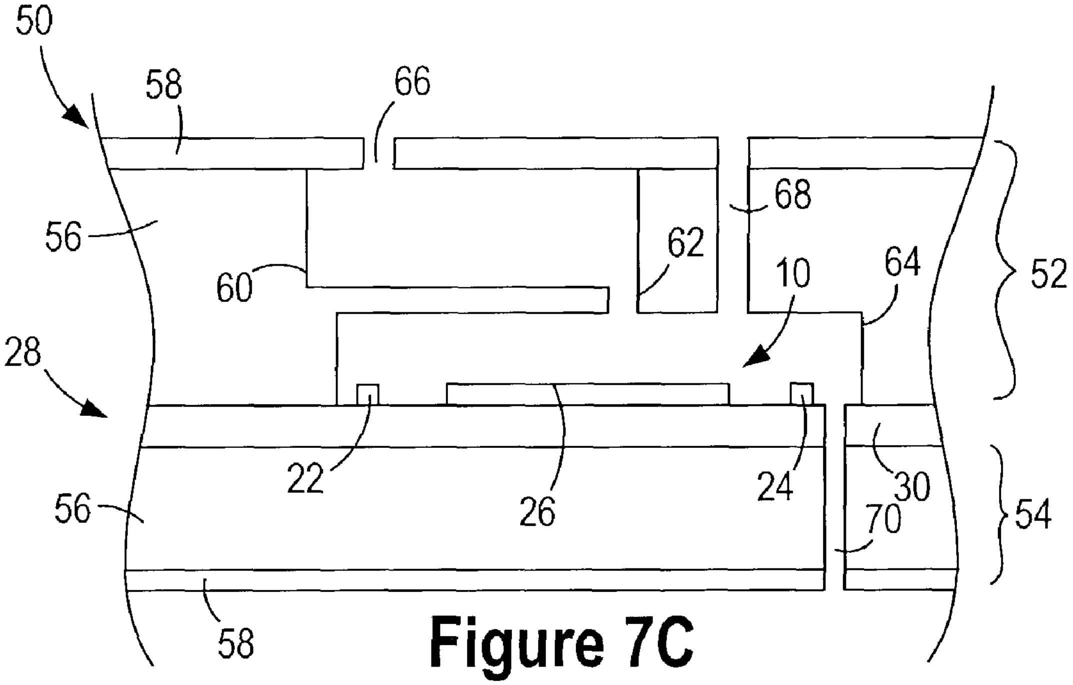
FIG. 7C is a cross section of the liquid transport structure taken along the line labeled B in FIG. 7A.

A sensor structure 28 can be included in a liquid transport structure 50 for use in transporting a liquid to one or more sensors 10 included on the sensor structure 28. FIG. 7A through FIG. 7C illustrate an example of a liquid transport structure 50 including a sensor structure 28. FIG. 7A is a topview of a liquid transport structure 50. FIG. 7B is a sideview of the liquid transport structure 50 taken in the direction of the line labeled A in FIG. 7A. FIG. 7C is a cross section of the liquid transport structure 50 taken along the line labeled B in FIG. 7A.

The liquid transport structure 50 includes a first member 52 and a second member 54 configured to hold the sensor structure 28. The first member 52 and the second member 54 each include a base 56 and a cover 58. A suitable material for the first member 52 and the second member 54 includes, but is not limited to, acrylic plastics and polymers. In some instances, the liquid transport structure 50 has a compact size that is suitable for use in the field. For instance, the liquid transport structure 50 can have a volume less than 26 cubic inches, less than 16 cubic inches, 4 cubic inches or 1 cubic inch. Examples of suitable dimensions include, but are not limited to, a block that is about 2 inch by 1 inch by 0.5 inch, 2 inch by 2 inch by 1 inch or 4 inch by 4 inch by 1 inch.

The liquid transport structure 50 can employ a variety of mechanisms for immobilizing the components of the liquid transport structure 50 relative to one another. For instance, registration or alignment pins (not shown) can extend through the liquid transport structure 50 to keep the various components immobilized relative to one another. Each pin can extend through first member 52, the sensor structure 28 and the second member 54. The use of pins allows the liquid transport structure 50 components to be separated from one another although other mechanisms may permanently immobilize the various components of the liquid transport structure 50. Additionally or alternatively, the components of the liquid transport structure 50 can be immobilized using techniques such as ultrasonic bonding, welding and gluing with registration and alignment geometry on each component. Although the liquid transport structure 50 is shown as having a substantially block shape structure, the liquid transport structure 50 can have a variety of different shapes.

The portion of the sensor structure 28 having the pads 34 extends from the liquid transport structure 50. As a result, the sensor structure 28 can be interfaced with a coupler that connects the sensor structure 28 to electronics configured to operate each sensor 10 so as to detect a component in the liquid.

The first member 52 can include one or more reservoirs 60. Each reservoir 60 is configured to hold a liquid to be transported to one or more sensors 10 located on the sensor structure 28. The cross section shown in FIG. 7C illustrates the relative positions of a reservoir 60 and a sensor 10 positioned on the sensor structure 28. The dashed line in FIG. 7A shows the approximate location of the reservoir 60 within the first member 52. The base 56 of the first member 52 defines a portion of the reservoir 60 and the cover 58 of the first member 52 defines a portion of the reservoir 60. An inlet channel 66 extends through the cover 58 to the reservoir 60. Suitable volumes for the reservoir include, but are not limited to, volumes less than 1 μL, 100 μL or 10 mL and/or volumes greater than 1 nL, 10 μL or 1 mL.

The sensor structure 28 and the first member 52 define an assay chamber 64 over the sensor 10. An outlet channel 62 extends from the reservoir 60 to the assay chamber 64 through the first member 52. In some instances, the outlet channel 62 is sized so the surface tension of a liquid in the reservoir 60 prevents the liquid from flowing out of the reservoir 60 under the action of gravity. A vent channel 68 extends through the first member 52 to the assay chamber 64. The vent channel 68 can be employed to vent the assay chamber 64 when liquid flows into and/or out of the assay chamber 64. Additionally, a waste channel 70 extends from the assay chamber 64 through the sensor structure 28 and through the second member 54. The waste channel 70 can be employed as an outlet for excess liquid or as an outlet for wash fluids when a liquid is washed off a sensor 10.

During operation of the liquid transport structure 50, a positive pressure is applied to a liquid in the reservoir 60 so as to transport the liquid through the outlet channel 62 into the assay chamber 64. The pressure can be sufficient to transport the liquid through the outlet channel 62, into the assay chamber 64 and onto the sensor 10. The positive pressure can be generated by increasing the pressure in the inlet channel 66 and/or by sealing the waste channel 70 while decreasing the pressure in the vent channel 68.

Figure 7D:
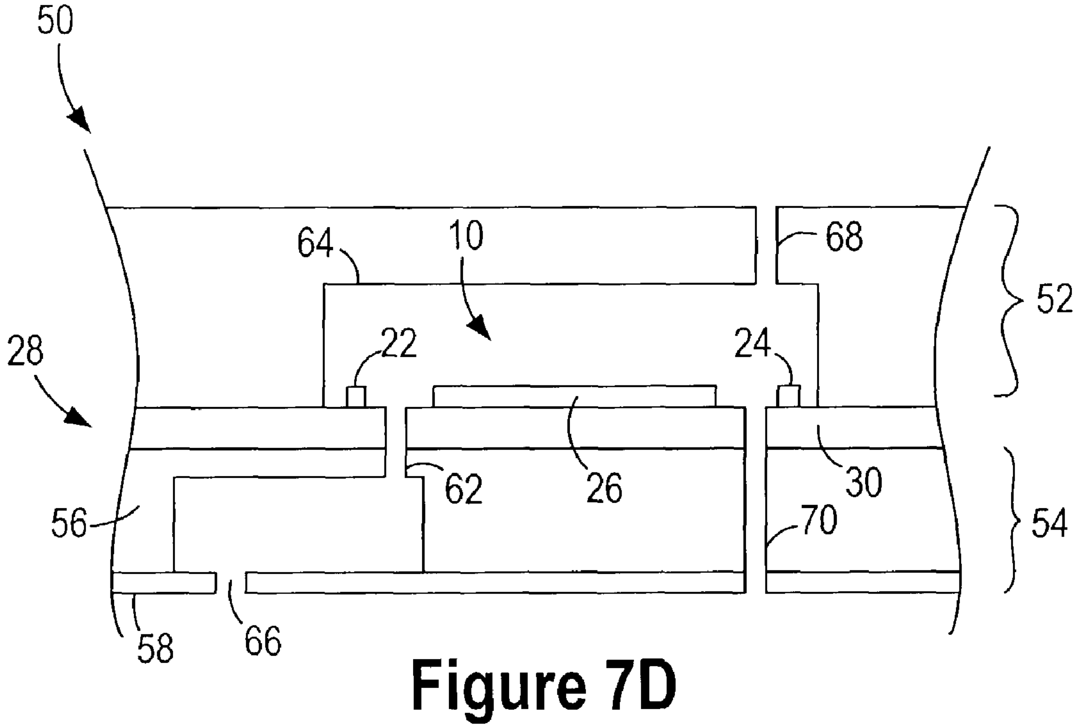
FIG. 7D is a cross section of a liquid transport structure having a reservoir positioned below the sensor structure.

The reservoir 60 can be positioned below the sensor structure 28 as shown in FIG. 7D. The base 56 of the second member 54 defines a portion of the reservoir 60 and the cover 58 of the second member 54 defines a portion of the reservoir 60. An inlet channel 66 extends through the cover 58 to the reservoir 60. A sensor 10 is positioned in an assay chamber 64 defined by the sensor structure 28 and the first member 52. An outlet channel 62 extends from the reservoir 60 to the assay chamber 64 through the base 56 of the second member 54 and through the sensor structure 28. During operation of a liquid transport structure 50 constructed according to FIG. 7D, a positive pressure is applied to a liquid in the reservoir 60 so as to transport the liquid through the outlet channel 62 into the assay chamber 64. The positive pressure can be generated by increasing the pressure in the inlet channel 66 and/or by sealing the waste channel 70 while decreasing the pressure in the vent channel 68. The volume of liquid transported into the assay chamber 64 can be sufficient to form a drop of the liquid on the working electrode 26. In some instances, the volume of liquid transported through the outlet channel 62 is sufficient to form a drop over the working electrode 26, the counter electrode 24 and the reference electrode 22 or to fill the assay chamber.

Each reservoir 60 can include more than one outlet channel 62 extending to an assay chamber 64. Increasing the number of outlet channels 66 can reduce the amount of pressure that is require to drive a liquid out of a reservoir 60 an into that assay chamber 64. In some instances, different outlet channels can extend from the same reservoir to different assay chambers.

Figure 7E:
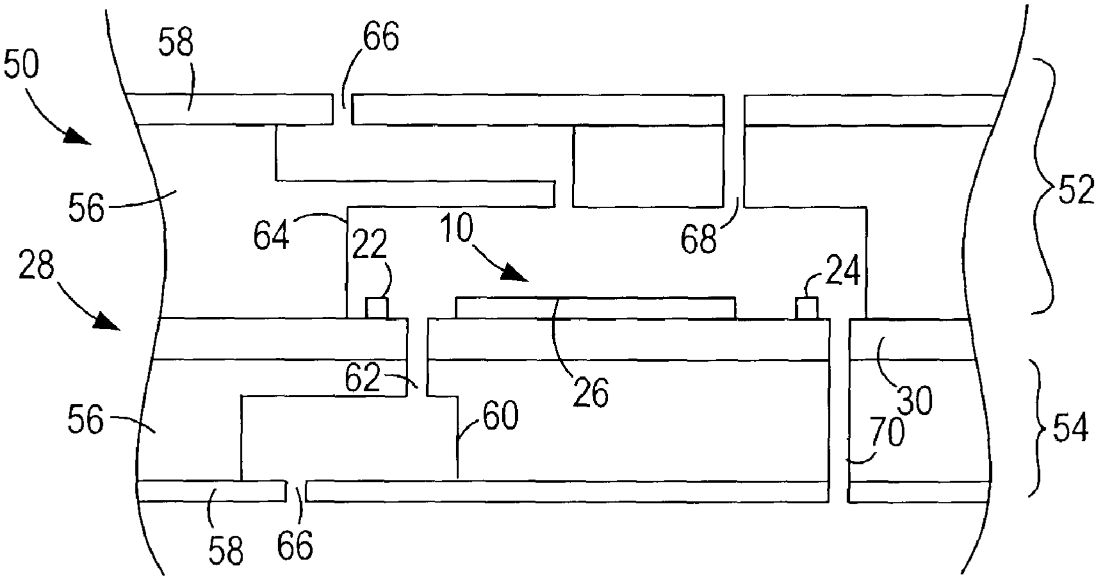
FIG. 7E is a cross section of a liquid transport structure having a reservoir positioned over the sensor structure and a reservoir positioned under the sensor structure.

The liquid transport structures 50 illustrated above can be combined to provide a liquid transport structure 50 having a reservoir 60 positioned over the sensor structure 28 and a reservoir 60 positioned under the sensor structure 28 as illustrated in FIG. 7E.

Figure 7F:
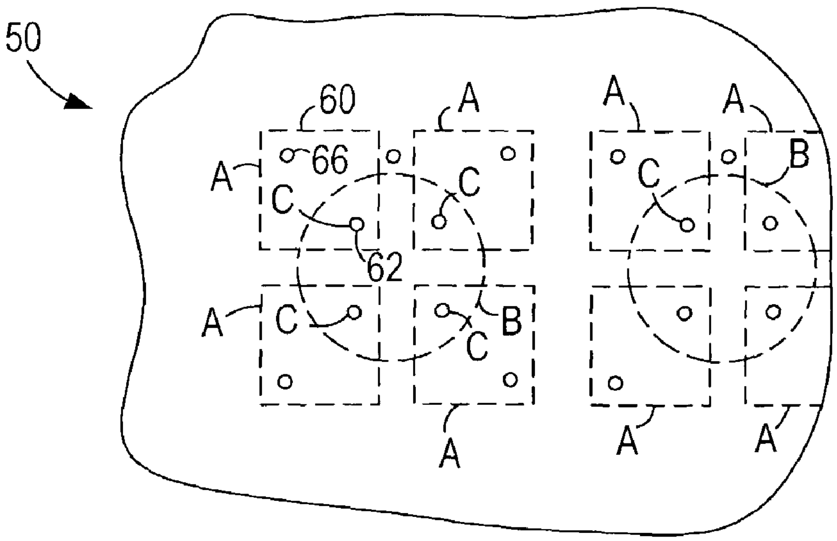
FIG. 7F is a topview of a portion of a liquid transport structure having a plurality of reservoirs configured to transport a liquid to a single sensor.

The first member 52 and/or the second member 54 can include a plurality of reservoirs 60 configured to transport a liquid to a single sensor 10. For instance, FIG. 7F is a topview of a portion of a liquid transport structure 50. The dashed line labeled B illustrates the location of a sensor 10 in the liquid transport structure 50. The dashed lines labeled A each illustrate the location of a reservoir 60 configured to transport a liquid onto the working electrode 26. The lines labeled C each illustrate the location of an outlet channel 62 associated with one of the reservoirs 60. Constructing the liquid transport structure 50 such that the first member 52 and/or the second member 54 include a plurality of reservoirs 60 configured to transport a liquid to a sensor 10 can increase the number of liquids that can be transported onto a single sensor 10.

Although FIG. 7A through FIG. 7F illustrate the liquid transport structure 50 employed in conjunction with a sensor structure 28 according to FIG. 2A through FIG. 2C, the liquid transport structure 50 can be employed with a sensor structure 28 according to FIG. 1D and FIG. 1E.

Figure 8:
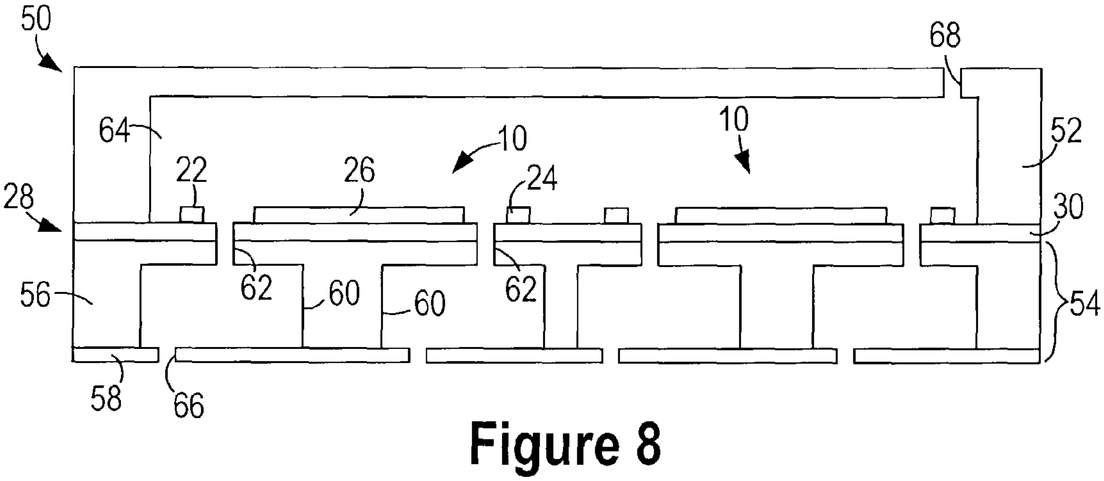
FIG. 8 is a cross section of an embodiment of a liquid transport structure having a common chamber over a plurality of sensors.

FIG. 8 is a cross section of another embodiment of a liquid transport structure 50. The first member 52 defines a common assay chamber 64 over a plurality of sensors 10. The first member 52 includes a vent channel 68. The second member 54 includes a plurality of reservoirs 60. Each reservoir 60 includes an outlet channel 62 configured to transport a liquid onto a particular sensor 10. Each sensor 10 can receive a liquid from more than one reservoir 60.

An inlet channel 66 extends from each reservoir 60. Before operation of the liquid transport structure 50, each inlet channel 66 can be maintained at a same pressure that is less than or equal to the pressure in the vent channel 68 to prevent flow of a liquid from a reservoir 60 into the assay chamber 64. During operation of the liquid transport structure 50, a liquid from a particular reservoir 60 can be transported onto a particular sensor 10 by increasing the pressure in the inlet channel 66 of that reservoir 60 above the pressure in the vent channel 68. The relative pressure can be increased by increasing the pressure in an inlet channel 66 and/or by reducing the pressure in the vent channel 68.

Figure 9A:
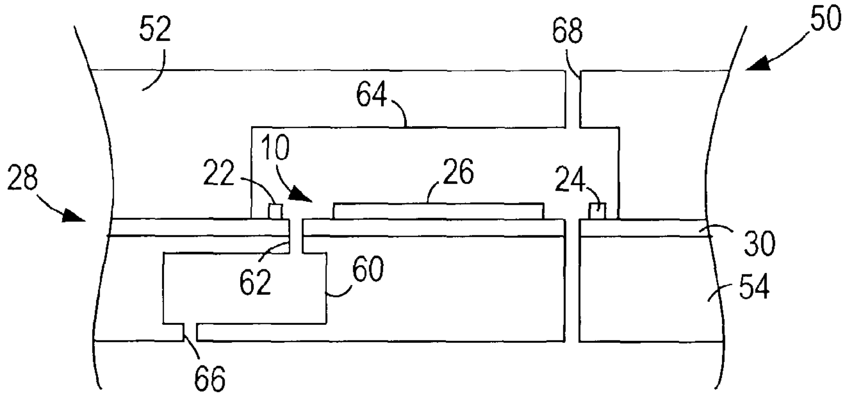
FIG. 9A is a cross section of the liquid transport structure shown in FIG. 7C where the first member and the second member each have a one-piece construction.

In some instances, the first member 52 and/or the second member 54 are not constructed with a base 56 and a cover 58. For instance, the first member 52 and/or the second member 54 can have a one-piece construction. FIG. 7D illustrates the first member 52 constructed as a single piece. Further, FIG. 9A is a cross section of the liquid transport structure 50 shown in FIG. 7C where the first member 52 and the second member 54 each have a one-piece construction. In some instances, the first member 52 and/or the second member 54 are constructed by immobilizing various components of the liquid transport structure relative to one another using techniques such as gluing, ultrasonic bonding, taping, welding and pressing.

Figure 9B:
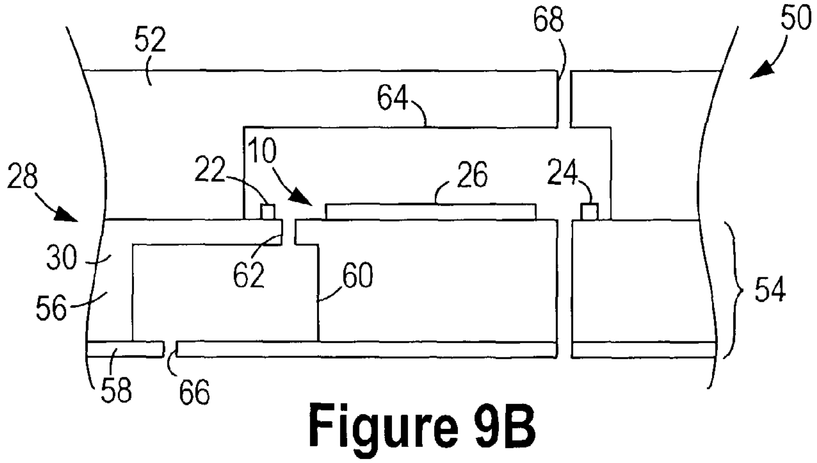
FIG. 9B is a cross section of a liquid transport structure having a second member that serves as the sensor support.
Figure 9C:
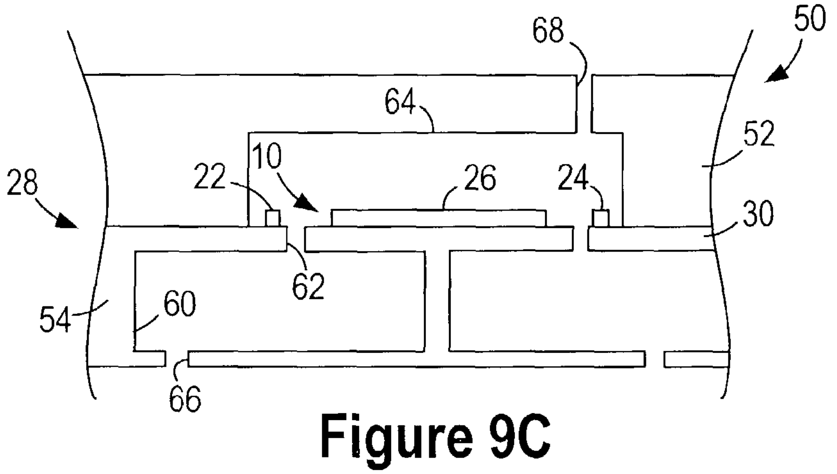
FIG. 9C is a cross section of a liquid transport structure where the first member and the second member each have a one-piece construction and where the second member serves as a sensor support.

In some instances, the sensor structure 28 is not independent of the liquid transport structure 50. For instance, the second member 54 can serve as the sensor support 30 or the sensor support 30 can be constructed to serve as the second member 54. FIG. 9B is a cross section of a liquid transport structure 50 having a second member 54 that serves as the sensor support 30. FIG. 9C is a cross section of a liquid transport structure 50 where the first member 52 and the second member 54 each have a one-piece construction and where the second member 54 serves as a sensor support 30.

Figure 9D:
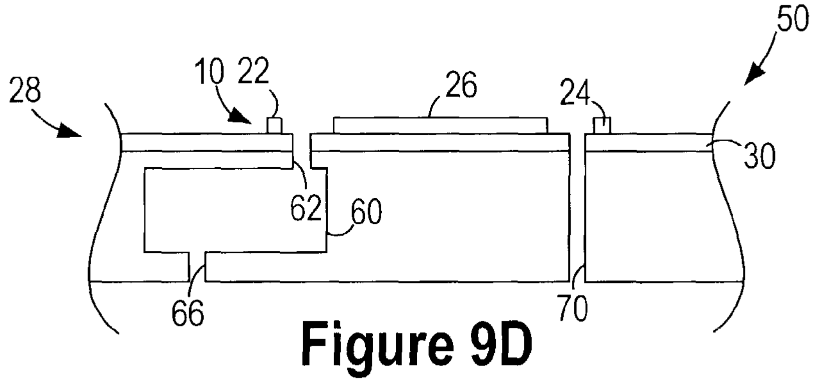
FIG. 9D is a cross section of a liquid transport structure that does not include a second member.

In some instances, the liquid transport structure 50 does not include a second member 54. FIG. 9D is a cross section of a liquid transport structure 50 that does not include a second member 54. A liquid can be transported from the reservoir 60 onto the sensor 10 by increasing the pressure in the inlet channel 66.

Many of the liquid transport structures 50 above are shown as having both a vent channel 68 and a waste channel 70. In some instances, the vent channel 68 also serves as a waste channel 70 and the liquid transport structure 50 does not include a waste channel 70. In some instances, the waste channel 70 also serves as a vent channel 68 and the liquid transport structure 50 does not include a vent channel 68.

Figure 10A:
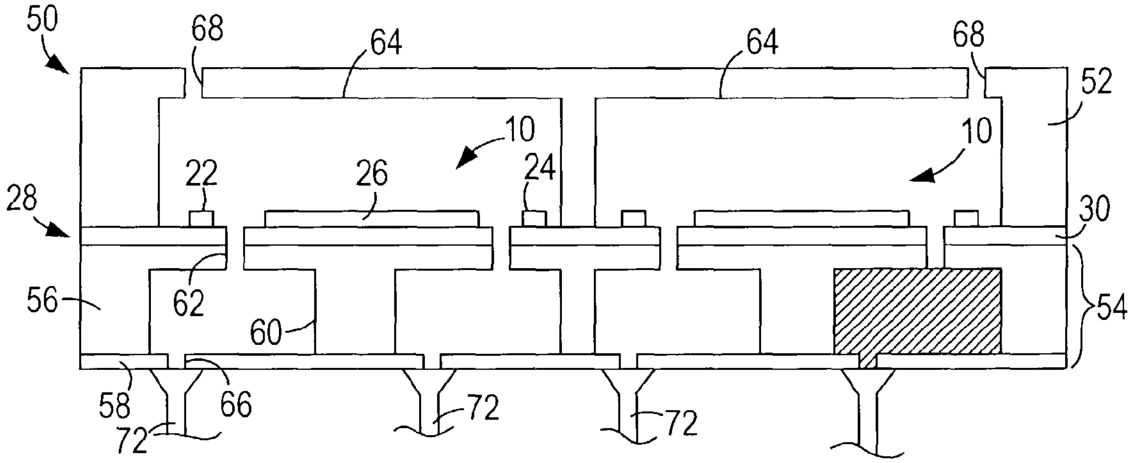
FIG. 10A is a cross section of a liquid transport structure having inlet channels sealed by a sealing mechanism. Each sealing mechanism can be operated so as to unseal and re-seal an inlet channel.
Figure 10B:
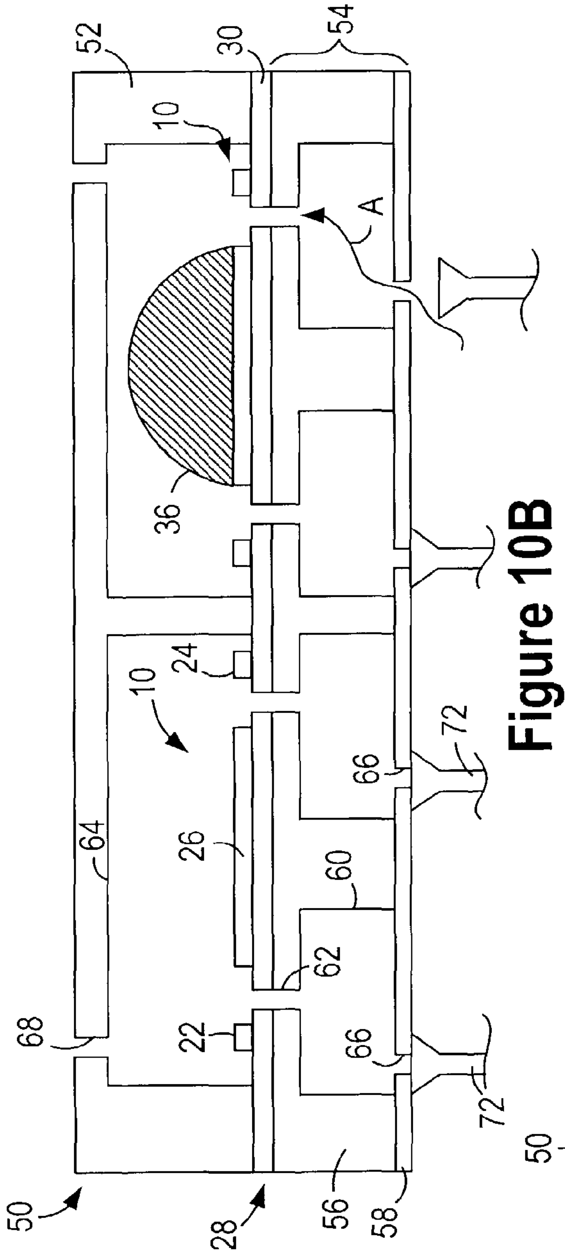
FIG. 10B is the liquid transport structure illustrated in FIG. 10A after one of the inlet channels has been unsealed.

As noted above, the liquid transports structures can be operated by controlling the pressure of one or more inlet channels 62 and one or more vent channels 68. FIG. 10A through FIG. 10B illustrate a system for controlling pressure in one or more inlet channels 62 and one or more vent channels 68. FIG. 10A is a cross section of a liquid transport structure 50 before a liquid is transported from a reservoir into an assay chamber. Each of the inlet channels 62 is sealed with a sealing mechanism 72 that can be operated so as to unseal and re-seal an inlet channel 66. A vacuum can be pulled on each of the vent channels 68 so the pressure in the assay chambers 64 is reduced below the ambient pressure. During operation of the liquid transport structure 50, a liquid from a particular reservoir 60 can be transported onto a particular sensor 10 by unsealing the inlet channel 66 in liquid communication with the particular channel. FIG. 10B is the liquid transport structure 50 illustrated in FIG. 10A after one of the inlet channels 62 has been unsealed. The pressure differential between the inlet channel 66 and the vent channel 68 draws the liquid from the reservoir 60 onto the sensor 10 as illustrated by the arrow labeled A in FIG. 10B. In some instances, the sealing mechanism 72 can be moved so as to re-seal the inlet channel 66 after the desired amount of liquid has been transported onto the sensor 10. Re-sealing the inlet channel 66 allows the liquid from another reservoir 60 in liquid communication with the same assay chamber 64 to be transported onto the same sensor 10.

A suitable sealing mechanism 72 is illustrated in FIG. 10A and FIG. 10B. Each sealing mechanism 72 includes a rod that can be moved into contact with the liquid transport structure 50 so as to seal an inlet channel 66. The rod can also be moved away from the liquid transport structure 50 so as to unseal an inlet channel 66. In some instances, the rod or the liquid transport structure 50 can include a gasket mechanism (not illustrated) positioned so as to form an airtight seal at the interface of the rod and the liquid transport structure 50. For instance, an O-ring can be seated on the rod such that the O-ring is positioned so as to surround an inlet channel 66 when the rod is moved into contact with the liquid transport structure 50.

Although FIG. 10A and FIG. 10B illustrate sealing mechanisms configured to seal inlet channels 62 by covering the opening of the inlet channel 66, a sealing mechanism can be constructed such that a portion of the sealing mechanism extends into the inlet channel 66 so as to plug liquid flow through the inlet channel 66. A gasket mechanism is often not required when a sealing mechanism is constructed so as to extend into the inlet channel 66.

Figure 10C:
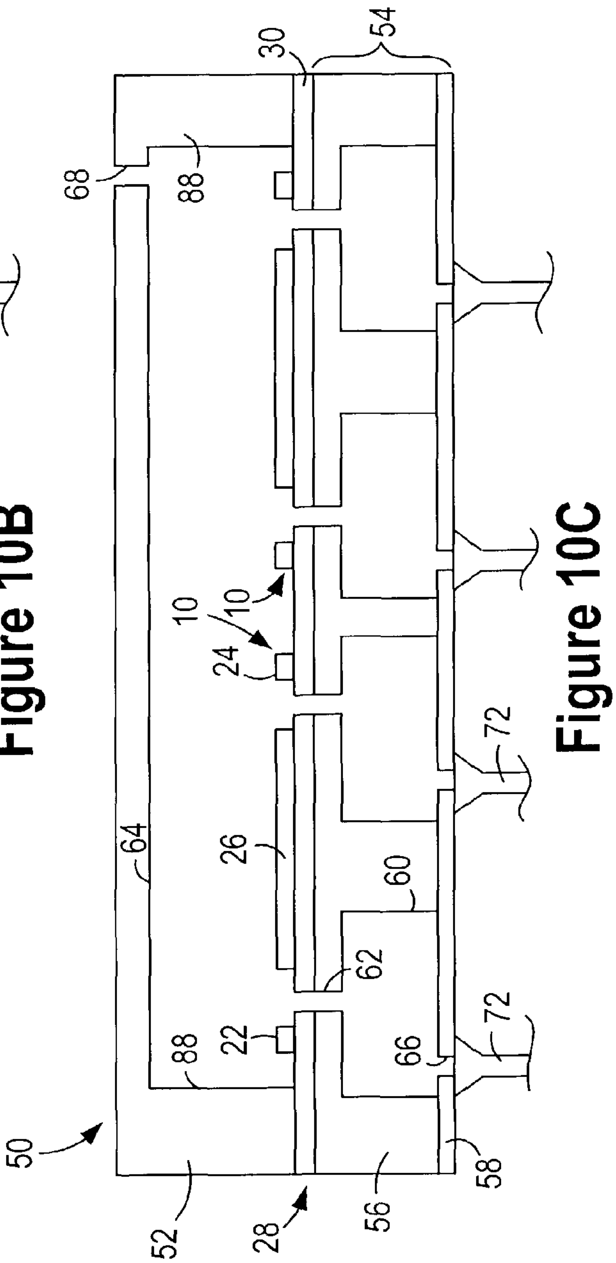
FIG. 10C is a cross section of a liquid transport structure having inlet channels sealed by a sealing mechanism. A common chamber is defined over a plurality of sensors.

As shown in FIG. 10C, the principle illustrated in FIG. 10A and FIG. 10B can be extended to a liquid transport structure 50 constructed according to FIG. 8. During operation of the liquid transport structure 50, a vacuum can be pulled on the vent channel 68 to reduce the pressure in the common assay chamber 64 relative to the ambient pressure. A liquid from a particular reservoir 60 can be transported onto a particular sensor 10 by unsealing the inlet channel 66 in liquid communication with the particular channel. The pressure differential between the common assay chamber 64 and the unsealed vent channel 68 draws the liquid from the reservoir 60 onto the sensor 10.

Although the principle of sealing and unsealing the inlet channels 62 are taught in the context of a liquid transport structure 50 having reservoirs 60 positioned under the sensors 10, the same principles can be applied to a liquid transport structure 50 having reservoirs 60 positioned over a sensor 10 as shown in FIG. 7C or to a liquid transport structure 50 having one or more reservoirs 60 positioned over a sensor 10 and one or more reservoirs 60 positioned under a sensor 10 as shown in FIG. 7E.

Figure 11A:
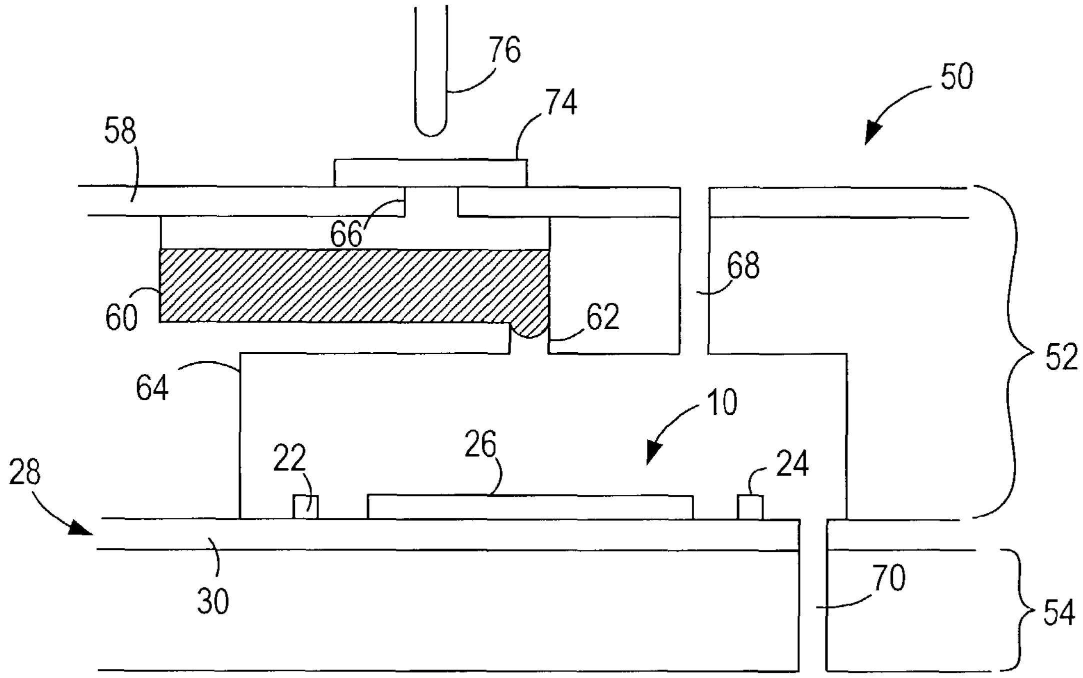
FIG. 11A is a cross section of a liquid transport structure having a diaphragm obstructing an inlet channel.

The liquid transport structures shown above can include a diaphragm 74 obstructing an inlet channel 66. For instance, FIG. 11A is a cross sectional view of a liquid transport structure 50 having a diaphragm 74 obstructing an inlet channel 66. Although the diaphragm 74 is shown positioned over a port of the inlet channel 66, the diaphragm 74 can be positioned in the inlet channel 66. Suitable materials for a diaphragm 74 include, but are not limited to, latex, rubbers, silicon rubbers and polymers. A suitable method of immobilizing a diaphragm 74 relative to the liquid transport structure 50 includes, but is not limited to, gluing, ultrasonic bonding, taping, welding, epoxying and pressing.

Figure 11B:
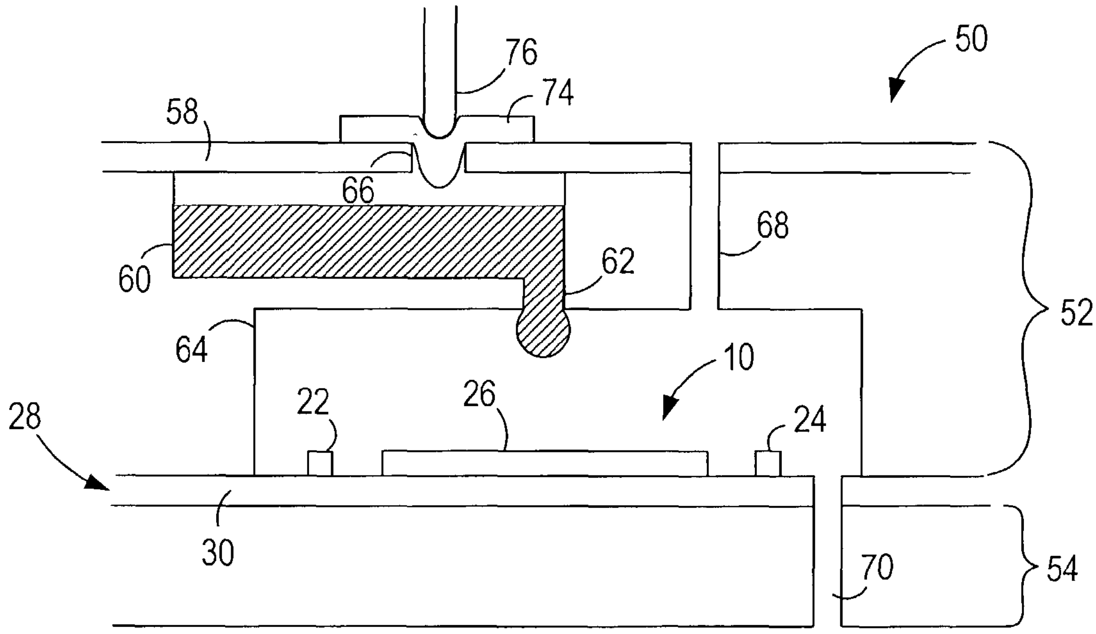
FIG. 11B is a cross section of a liquid transport structure having an instrument moved into contact with the diaphragm of FIG. 11A.

In some instances, a diaphragm is flexible. A flexible diaphragm 74 can be operated so as to control pressure on liquids within a liquid transport structure 50. For instance, an instrument 76 can be employed to drive the diaphragm 74 further into the inlet channel as shown in FIG. 11B. When the diaphragm is substantially impermeable to fluids, the movement of the diaphragm 74 into the inlet channel increases the pressure within the inlet channel 66 and can drive a liquid from the reservoir into the assay chamber 64.

Although the diaphragm 74 of FIG. 1A is shown as obstructing an inlet channel 66, a diaphragm 74 can be employed to obstruct other channels on the liquid transport structure 50. For instance, a diaphragm 74 can be employed to obstruct a waste channel 70 and/or a vent channel 68.

The diaphragm 74 can include one or more openings through which the fluid can flow. Example openings include, but are not limited to, pores, slits, holes, apertures. The size and number of the one or more openings can control the pressure required to drive a fluid through the diaphragm. For instance, reducing the size and/or number of the one or more openings can increase the pressure required to drive the fluid through the diaphragm. Suitable diaphragms having openings include, but are not limited to, passive valves, pinch holes, septa, filters and membranes.

Figure 11C:
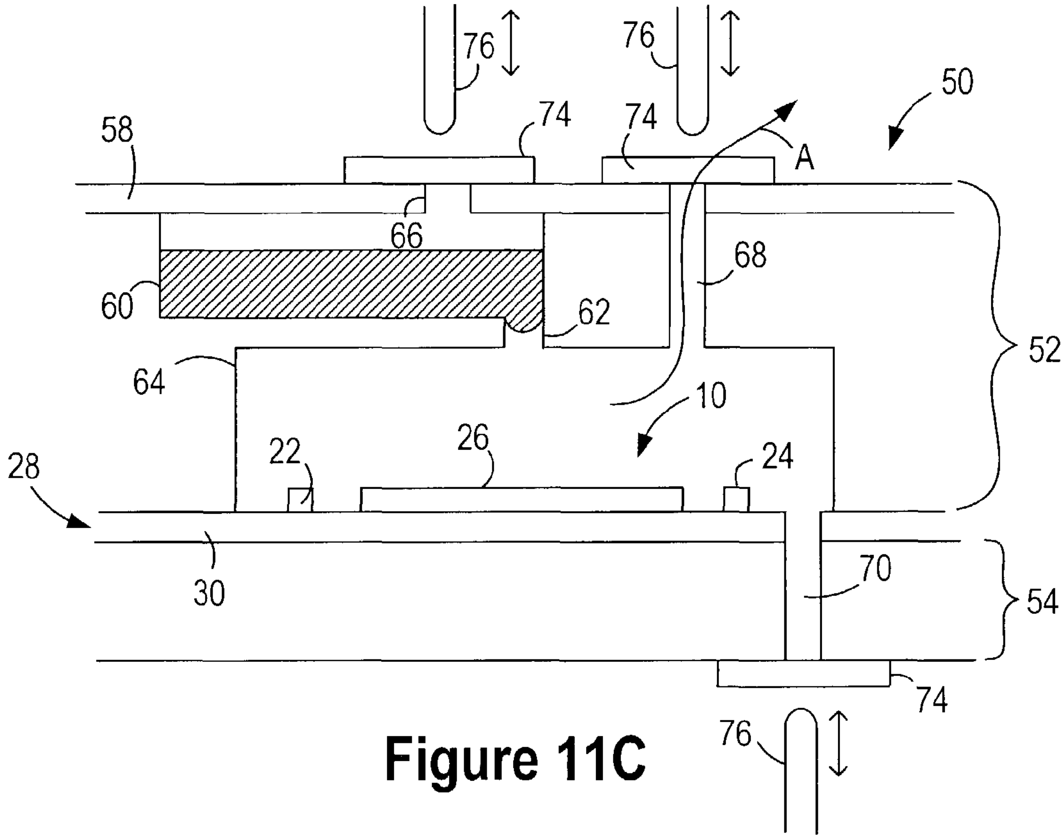
FIG. 11C is a cross section of a liquid transport structure having a diaphragm obstructing a vent channel. The diaphragm includes one or more openings through which a fluid can flow
Figure 11D:
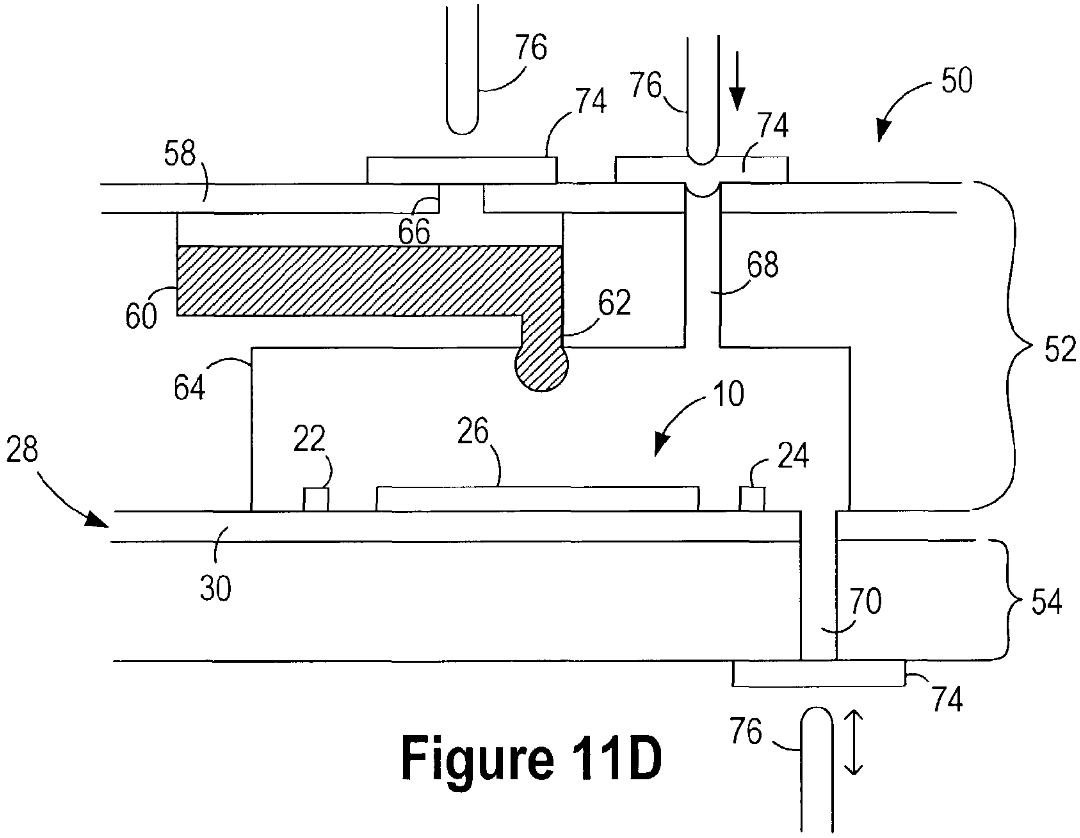
FIG. 11D is a cross section of a liquid transport structure having an instrument moved into contact with the diaphragm of FIG. 11C.

A diaphragm 74 having one or more openings through which a fluid can flow can be employed to control pressure in the assay chamber 64. For instance, FIG. 11C is cross section of a liquid transport structure 50 having a diaphragm 74 obstructing a vent channel 68. The one or more openings allow fluid in the assay chamber 64 to be vented through the vent channel 68 as shown by the arrow labeled A. An instrument 76 can be moved into contact with the diaphragm 74 to seal the vent channel 68. For instance, the arrow labeled A in FIG. 11D illustrates the instrument 76 shown in FIG. 11C moved into contact with the diaphragm 74. The instrument can seal the one or more openings in the diaphragm 74 or can close the one or more openings.

Although the above diaphragms are portrayed as being flexible, the diaphragm can be rigid.

Figure 11E:
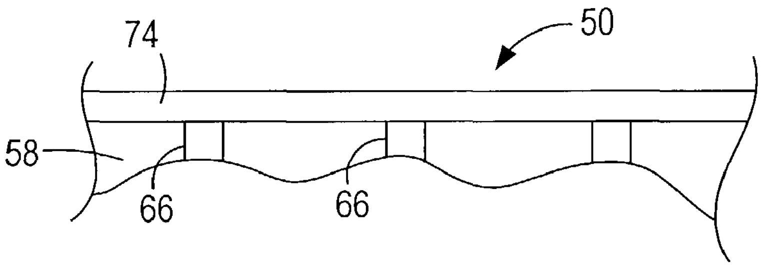
FIG. 11E is a cross section of a liquid transport structure having a diaphragm positioned so as to obstruct a plurality of channels.

The liquid transport structure can include a plurality of diaphragms 74. Different diaphragms 74 can obstruct different channels. Different diaphragms 74 can be positioned on different sides of the liquid transport structure 50. A single diaphragm 74 can obstruct more than one channel as illustrated in FIG. 11E. In some instances, the diaphragm 74 is layer of material that extends across a side of the liquid transport structure 50. The layer of material can include one or more openings aligned with channels that are not to be obstructed.

Figure 11F:
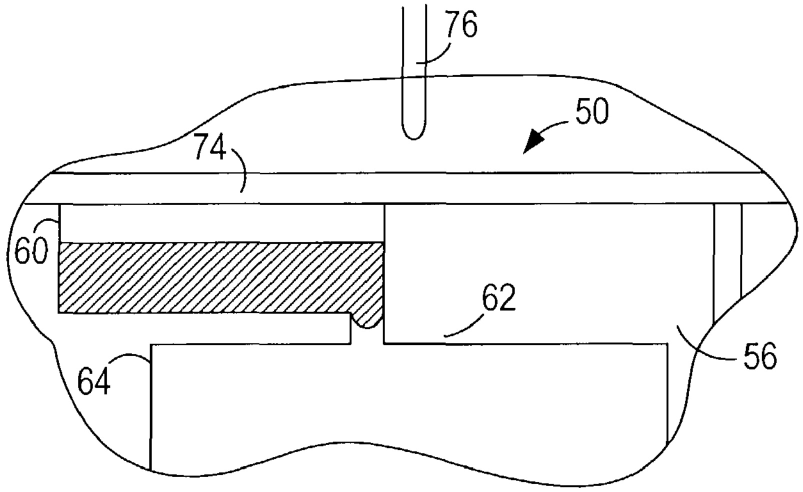
FIG. 11F is a cross section of a liquid transport structure having a reservoir. A diaphragm is positioned so as to cover the reservoir.
Figure 11G:
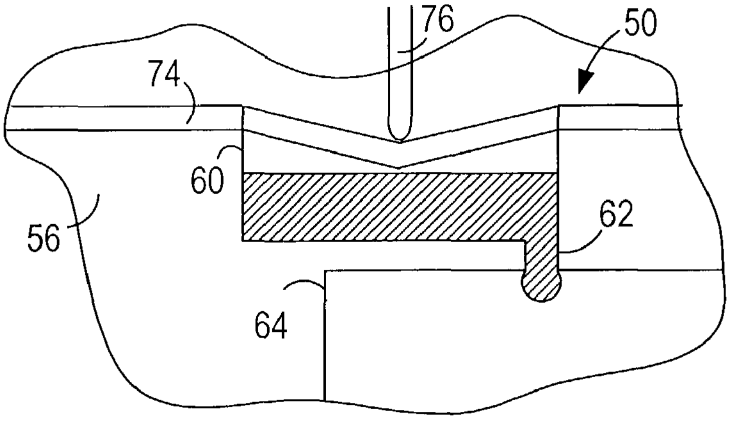
FIG. 11G is a cross section of a liquid transport structure having an instrument moved into contact with the diaphragm of FIG. 11F.

In some instances, a diaphragm 74 can be positioned so as to cover a reservoir 60. For instance, FIG. 11F is a cross section of a liquid transport structure 50. A diaphragm 74 extends across the top of a reservoir 60 so as to seal the top of the reservoir 60 to liquids within the reservoir 60. An instrument 76 can be employed to drive the diaphragm 74 into the reservoir 60 as shown in FIG. 11G. The movement of the diaphragm 74 into the reservoir 60 can drive a liquid from the reservoir 60 into the assay chamber 64. In some instances, the diaphragm 74 can extend across a side of a base so the diaphragm 74 serves as a cover 58 for a base of the first member or for a base of the second member.

Figure 12:
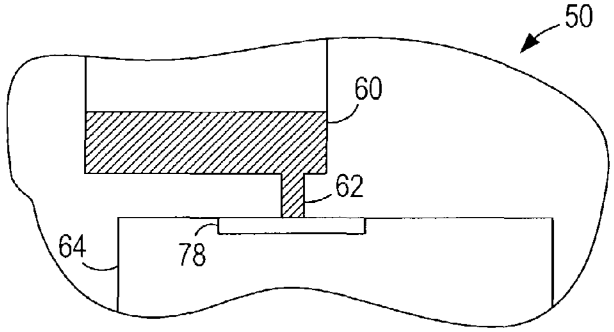
FIG. 12 is a cross section of a liquid transport structure having a reservoir with an outlet channel. An obstruction is positioned so as to obstruct the outlet channel.

One or more outlet channels 62 of a liquid transport structure can include an obstruction 78 as illustrated in FIG. 12. FIG. 12 is a cross section of a liquid transport structure having an obstruction 78 positioned over the outlet channel 62. Although the obstruction 78 is shown positioned over a port of the outlet channel 62, the obstruction 78 can be positioned in the outlet channel 62. Suitable materials for an obstruction 78 include, but are not limited to, latex, rubbers, silicon rubbers and polymers. A suitable method for immobilizing an obstruction 78 relative to the liquid transport structure includes, but is not limited to, gluing, ultrasonic bonding, taping, welding, epoxying and pressing.

The obstruction 78 can serve to constrain a liquid in a reservoir 60 by increasing the pressure required to drive a liquid from the reservoir 60 into the assay chamber 64. For instance, the obstruction 78 can include one or more openings through which the liquid can flow. Example openings include, but are not limited to, pores, slits, holes, apertures. The size and number of the one or more openings can control the pressure required to drive a liquid from the reservoir into the assay chamber. For instance, reducing the size and/or number of the one or more openings can increase the pressure required to drive the liquid into the assay chamber 64. A suitable obstruction 78 includes, but is not limited to, passive valves, pinch holes, septa, filters and membranes.

Figure 13A:
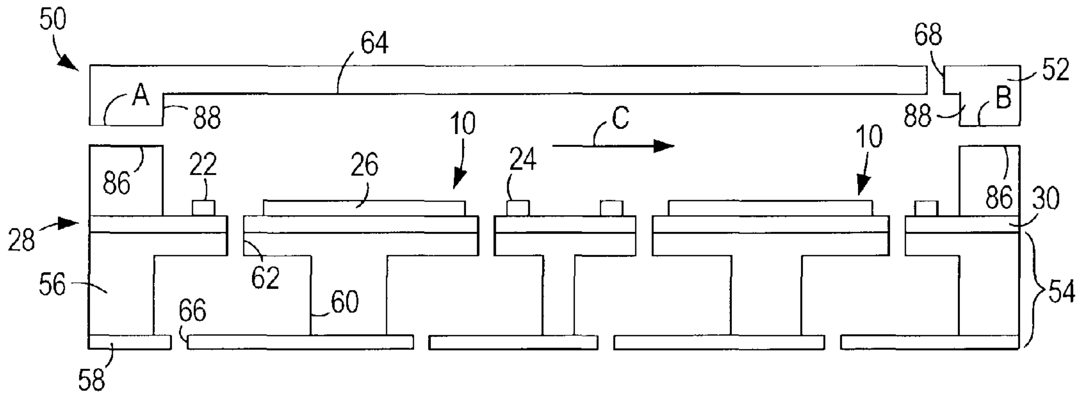
FIG. 13A is a cross section of a liquid transport structure configured to generate a liquid flow across a plurality of sensors. The liquid transport structure includes channels that each have a port in a lateral side of an assay chamber within the liquid transport structure.

The liquid transport structure 50 can include one or more channels 86 configured to flow a liquid across one or more sensors 10 held in a liquid transport structure 50. FIG. 13A is a cross section of a liquid transport structure 50 configured to generate a shear flow across a plurality of sensors 10. Channels 86 are formed in the liquid transport structure 50 such that ports of different channels 86 are located on opposing lateral sides 88 of the assay chamber 64. Flowing a liquid through the channel 86 labeled A to the channel 86 labeled B causes the liquid to flow through the assay chamber 64 as shown by the arrow labeled C. The liquid can be flowed so as to generate a flow pattern that is substantially parallel to the upper surface of the working electrode 26. For instance, the liquid can be flowed through the assay chamber 64 so as to generate a shear pattern at the sensors 10.

Although FIG. 13A illustrates a plurality of sensors 10 positioned in the assay chamber 64, the channels 86 can be employed in conjunction with a liquid transport structure 50 having a single sensor positioned in an assay chamber 64.

Figure 13B:
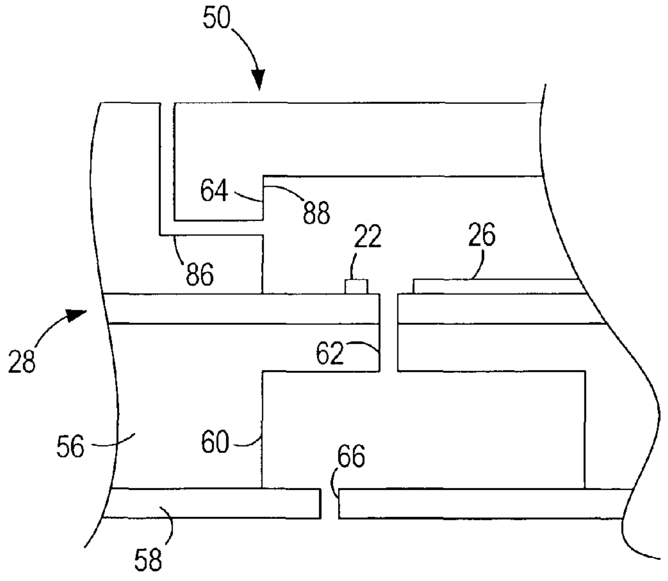
FIG. 13B is a cross section of a liquid transport structure having a channel with one port on a upper side of the liquid transport structure and another port positioned in a lateral side of an assay chamber positioned within the liquid transport structure.
Figure 13C:
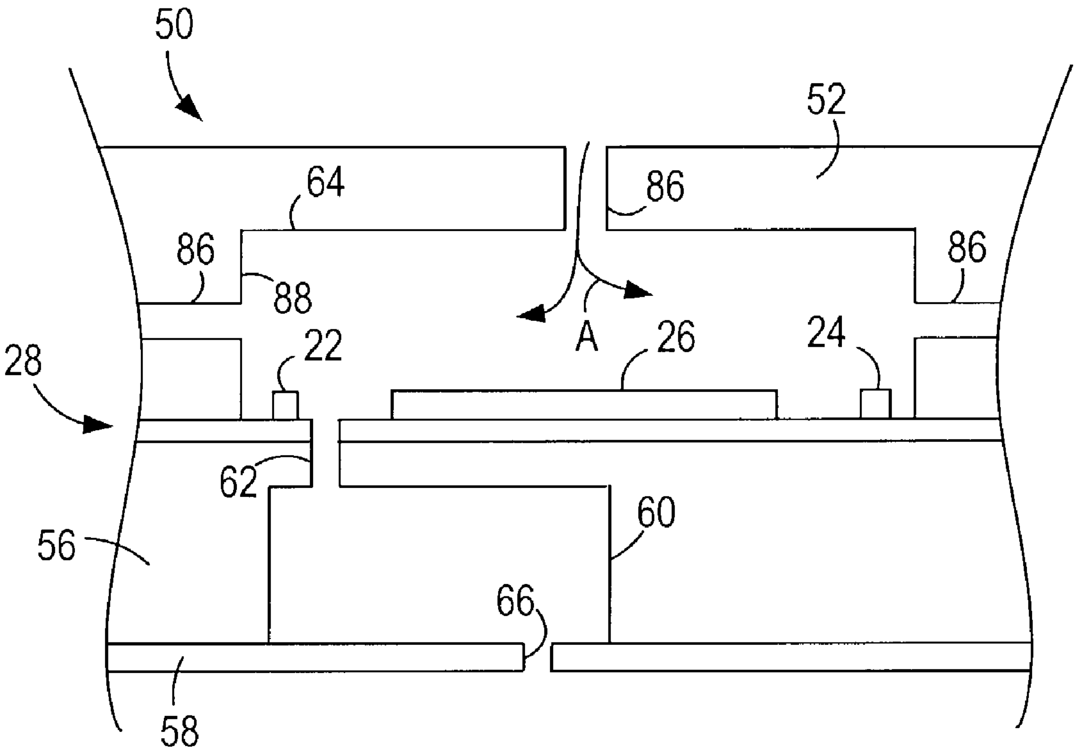
FIG. 13C is a cross section of a liquid transport structure configured to generate a liquid flow across a plurality of sensors. The liquid transport structure includes a channel extending through an upper side of the liquid transport structure.

One of more of the channels 86 can be constructed to have a port positioned on the upper side of the liquid transport structure 50 and/or on the lower side of the liquid transport structure 50. For instance, FIG. 13B is a cross section of a liquid transport structure 50 having a channel 86 with one port on the upper side of the liquid transport structure 50 and another port on the lateral side 88 of the assay chamber 64. Having a port on the upper side of the liquid transport structure 50 or on the lower side of the liquid transport structure 50 allows the channel 86 to be accessed using the same mechanisms as other channels with ports on the same side of the liquid transport structure 50.

One of more of the channels 86 can be constructed without a port positioned in the upper side of the assay chamber. For instance, FIG. 13B is a cross section of a liquid transport structure 50 having a channel 86 with a port on the upper side of the assay chamber. The channel allows the liquid to be flowed onto a sensor 10 from over the sensor 10 as illustrated by the arrow labeled A. Alternatively, the direction of the liquid flow can be reversed. Although not illustrated, a channel 86 can be constructed with a port positioned in the lower side of the assay chamber. As a result, the liquid can be flowed up into the assay chamber.

The flow of a liquid across a sensor can reduce noise associated with operation of the liquid transport structure 50. As noted above, a target agent is generally bonded to the surface of the sensor 10 or to the sensor support 30 during operation of a sensor 10. Non-specific binding of other agents to the sensor 10 and/or the sensor support 30 can act as a source of noise. Non-target agents are generally bound with less affinity or weaker bond than the target agent. As a result, the flow of a liquid across the sensors can cause the non-target agents to detach while the target agents remain intact. The ability to detach these non-target agents from the sensor 10 and/or from the sensor support 30 can serve to reduce the noise associated with operation of the sensors 10.

Figure 13D:
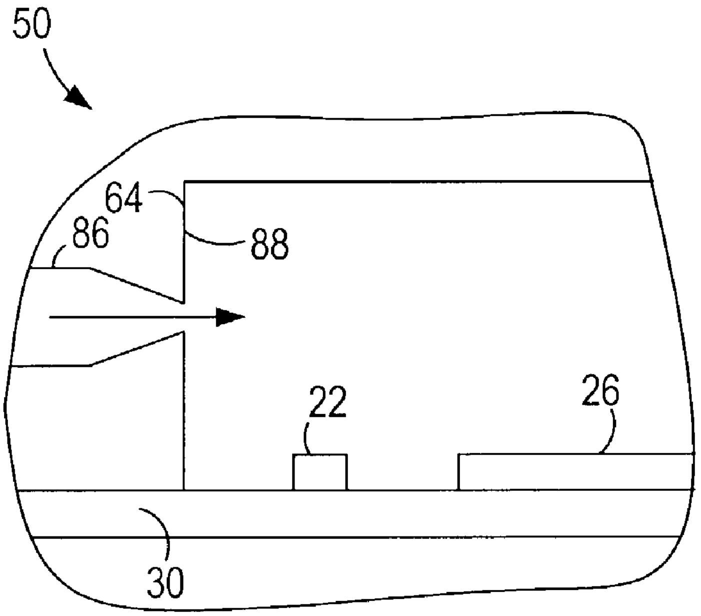
FIG. 13D is a cross section of a channel configured to serve as a nozzle.

A channel 86 can be configured to act as a nozzle. FIG. 13D is a cross section of a liquid transport structure 50 having a channel 86 configured to serve as a nozzle. The cross sectional area of the channel decreases up to the port. The nozzle can increase the speed of the liquid flow into the assay chamber and can accordingly increase the force of the liquid on the non-target agents. As a result, the nozzle structure can remove additional non-target agent from the sensor.

Although FIG. 13 illustrates a single channel 86 through opposing lateral sides 88 of the liquid transport structure 50, a lateral side 88 of the liquid transport structure 50 can include more than one channel 86. Further, the channel 86 can be formed in more that two of the lateral sides 88.

Figure 14A:
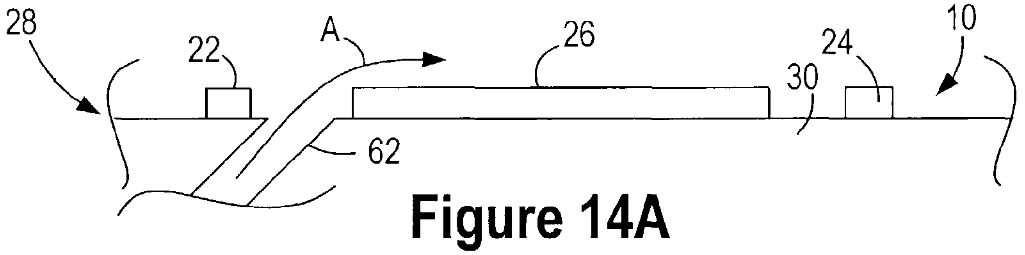
FIG. 14A illustrates an outlet channel configured to direct a liquid flowing from the outlet channel onto the working electrode of a sensor.
Figure 14B:
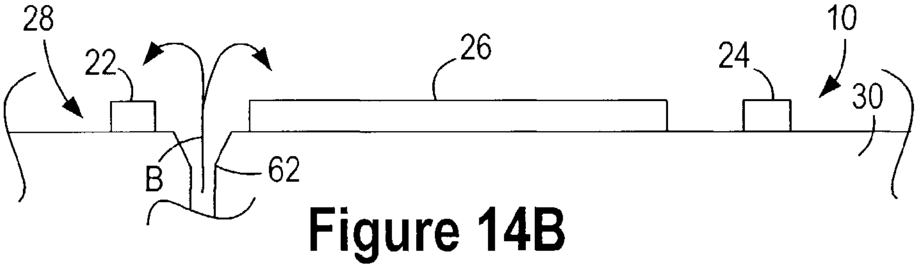
FIG. 14B illustrates an outlet channel configured to direct a liquid flowing from the outlet channel onto the working electrode, the reference electrode and the counter electrode of a sensor.

The outlet channels 66 of the liquid transport structures 50 shown above can be constructed so as to provide a particular flow of liquid onto a sensor 10. For instance, when a reservoir 60 is positioned below a sensor 10, the outlet of an outlet channel 62 can be angled toward the working electrode 26 as shown in FIG. 14A. The angle of the outlet channel 62 can enhance the flow of a liquid onto the working electrode 26 as illustrated by the arrow labeled A. The outlet channel 62 can also flare toward the working electrode 26 and the reference electrode 22 or toward the working electrode 26 and the counter electrode 24 as illustrated in FIG. 14B. The outlet channel 62 illustrated in FIG. 14B facilitates the flow of the liquid over the working electrode 26 and the counter electrode 24 as shown by the arrow labeled B.

When a reservoir 60 is positioned under the sensors 10, the above illustrations show the outlet of the outlet channel 62 positioned between the working electrode 26 and the reference electrode 22 or between the working electrode 26 and the counter electrode 24. However, the outlet of the outlet channel 62 can be positioned elsewhere relative to the sensor 10. For instance, the outlet can be positioned between the reference electrode 22 and the counter electrode 24. Alternatively, the outlet can be positioned such that the outlet and the working electrode 26 are on opposite sides of the reference electrode 22. Further, the outlet can be positioned such that the outlet and the working electrode 26 are on opposite sides of the reference electrode 22.

Figure 15A:
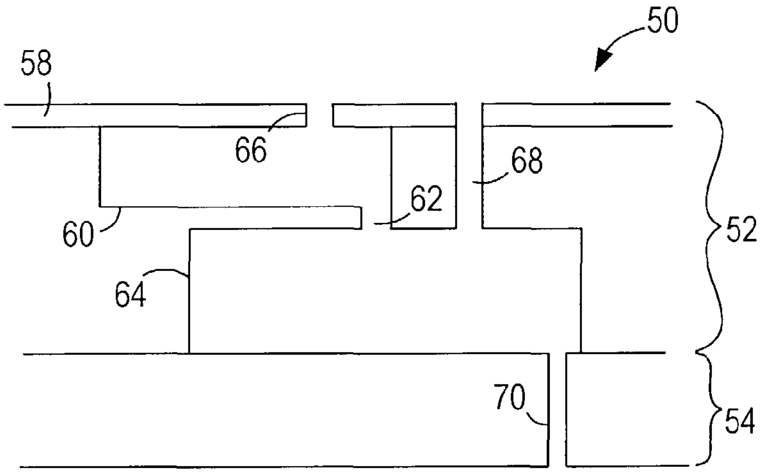
FIG. 15A is a cross section of a liquid transport structure having an assay chamber without a sensor.

The liquid transport structures illustrated above need not include sensors. For instance, the liquid transport structures illustrated above can be assembled without a sensor structure. As a specific example, FIG. 15A illustrates the liquid transport structure of FIG. 7C assembled without a sensor structure. The assay chamber 64 can serve as a mixing chamber. For instance, liquids can be transported into the assay chamber from different reservoirs 60. Accordingly, the liquids from different reservoirs are mixed together in the assay chamber 64. When one or more channels include a diaphragm 74, the diaphragm 74 can be manipulated so as to agitate and further mix the liquids in the mixing chamber. The pressure in the mixing chamber can be increased so as to drive the mixed liquids through the waste channel 70 where the mixed liquids can be employed in other applications.

Figure 15B:
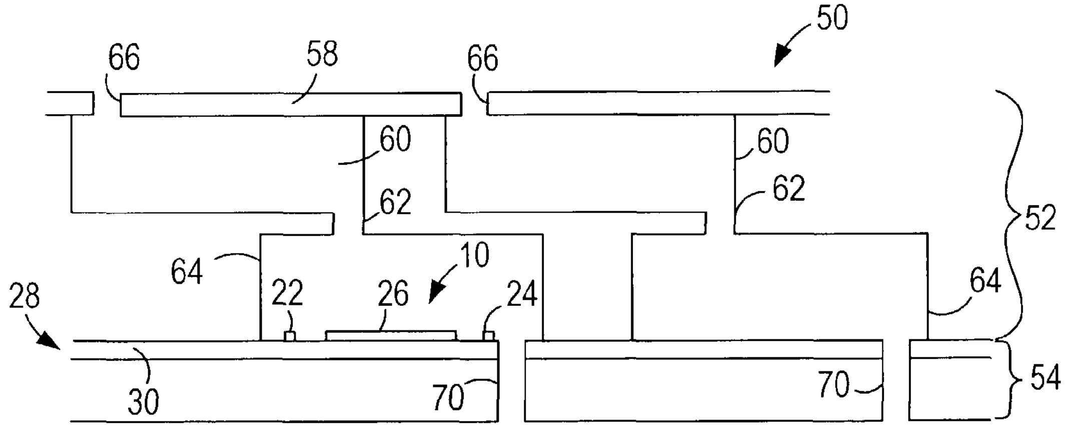
FIG. 15B is a cross section of a liquid transport structure having an assay chamber without a sensor and an assay chamber with a sensor.

The liquid transport structure 50 can include one or more assay chambers 64 that serve as a mixing chamber and one or more assay chambers 64 having one or more sensors. For instance, FIG. 15B is a cross section of a liquid transport structure 50 having a plurality of assay chambers 64. Sensors 10 are arranged on the sensors structure 28 such that a sensor 28 is present in one assay chamber 64 but is not present in another assay chamber 64. The assay chamber 64 that does not include a sensor can be operated as a mixing chamber.

Figure 16A:
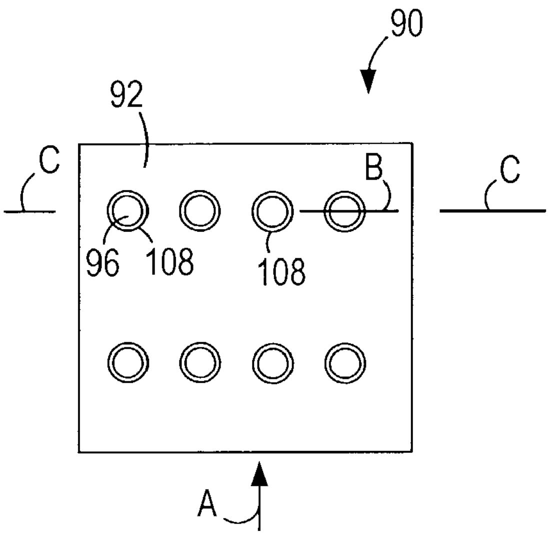
FIG. 16A is a topview of an interface system configured to serve as an interface between a liquid transport structure and pressure control devices such as pumps, vacuums and valves.
Figure 16B:
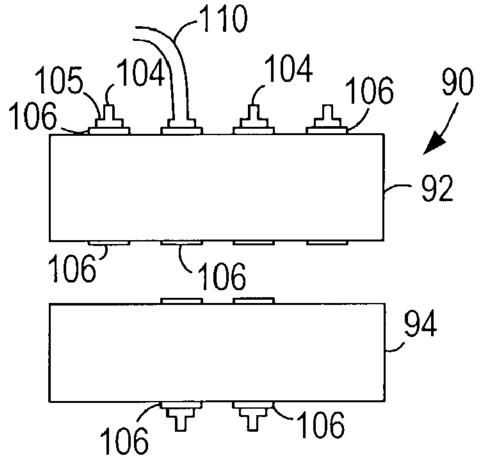
FIG. 16B is a sideview of the interface system looking in the direction of the arrow labeled A in FIG. 16A.
Figure 16C:
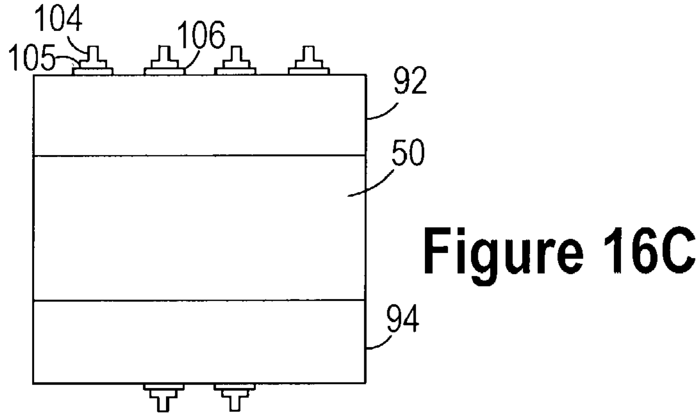
FIG. 16C is a sideview of a liquid transport structure positioned between the first interface member and the second interface member of FIG. 16B.
Figure 16D:
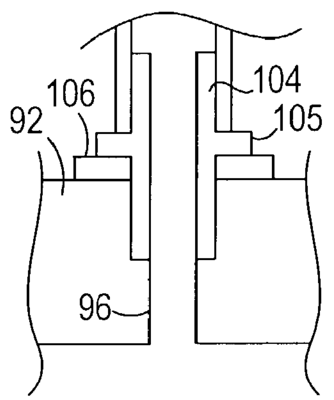
FIG. 16D is a cross section of the interface member taken along the line labeled B in FIG. 16A.
Figure 16E:
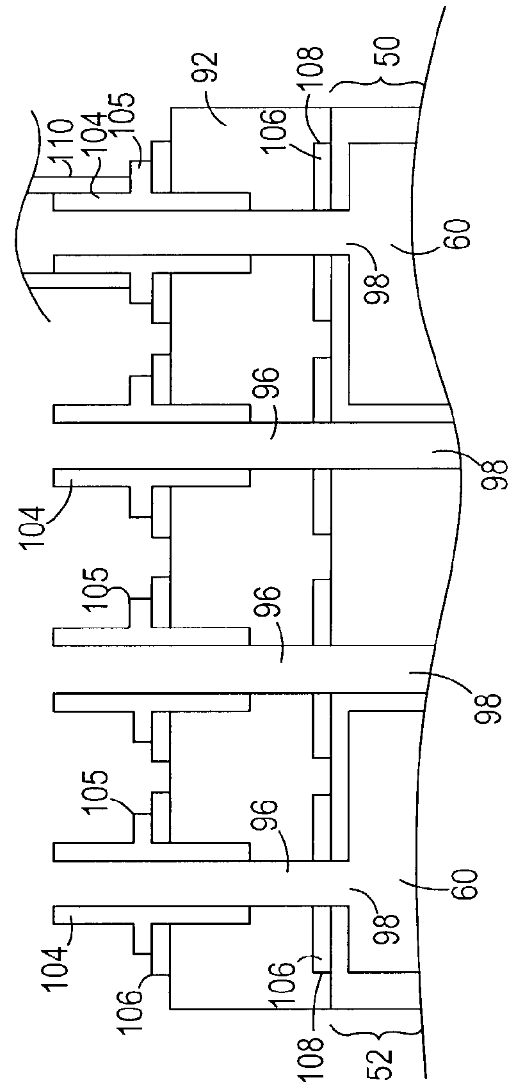
FIG. 16E is a cross section of the interface member illustrated in FIG. 16A taken between the lines labeled C. The interface member of FIG. 16E is shown coupled with the first member of the liquid transport structure of FIG. 7C.

As noted above, a liquid is transported from a reservoir 60 into an assay chamber by generating a pressure differential across a reservoir 60. The pressure in a channel can be controlled with the use of pressure sources such as pumps and vacuums. FIG. 16A through FIG. 16E illustrate an interface system 90 that can be employed to provide liquid communication between each reservoir 60 and a pump and/or a vacuum. FIG. 16A is a topview of an interface system 90 configured to be employed with a liquid transport structure 50. FIG. 16B is a sideview of the interface system 90 illustrated in FIG. 16A looking in the direction of the arrow labeled A. The interface system 90 includes a first interface member 92 and a second interface member 94. FIG. 16C is a sideview of a liquid transport structure 50 positioned between the first interface member 92 and the second interface member 94 of FIG. 16B. FIG. 16D is a cross section of the interface member seen in FIG. 16A taken along the line labeled B. FIG. 16E is a cross section of the interface member illustrated in FIG. 16A taken between the lines labeled C. The interface member of FIG. 16E is shown coupled with the first member 52 of the liquid transport structure 50 of FIG. 7C.

The liquid transport structure 50 can be interfaced with assay equipment by clamping the liquid transport structure 50 between interface members as shown in FIG. 16C. The interface between the first liquid transport structure 50 member and an interface member is shown in FIG. 16E. A suitable material for construction of the interface members includes, but is not limited to, acrylic plastics. The interface members include one or more lumens 96 configured to be aligned with the channels 98 on the adjacent liquid transport structure 50 member. The channels 98 with which the lumens 96 are aligned can include inlet channels, outlet channels, vent channels and waste channels. Each lumen 96 includes a narrow section and a broad section. A connector 104 is inserted into the broad section of the lumen 96. A suitable material for construction of the connector 104 includes, but is not limited to, metals, hard plastics and polymers. The connector 104 includes a flange 105. A gasket mechanism 106 such as an O-ring is positioned between the interface member and the flange 105. The gasket mechanism 106 serves to seal the connection between the connector 104 and the interface member.

The interface members also include recesses 108 configured to seat a gasket mechanism 106 around the opening of a lumen 96. A suitable gasket mechanism 106 includes, but is not limited to, an O-ring. As is evident in FIG. 16E, the gasket mechanism 106 seated in the recesses 108 seals the connection between the liquid transport structure 50 member and the interface member.

The connectors 104 can each be coupled with a tube 110 as illustrated in FIG. 16B, and FIG. 16E. Although a single connector 104 is shown as being coupled with a tube 110, a plurality of the connectors 104 can be coupled with a tube 110. In some instances, each of the connectors 104 is coupled with a tube 110. The narrow section of the lumen 96 extends through the connector 104 and the tube 110. Additionally, the narrow section of the lumen 96 is aligned with a channel 98 through the liquid transport structure 50 member. Accordingly, liquid from the tube 110 can flow from or into the channel 98 in the liquid transport structure 50 member. As a result, the interface system 90 serves to provide liquid communication between the tubes 110 and channels 98 in the liquid transport structure 50. The assay equipment can include vacuums and/or pumps in liquid communication with the tubes 110. The vacuums and/or pumps can be employed to control the pressures in the various channels 98 of the liquid transport structure 50. The assay equipment can include valves in communication with the tubes 110. Each valve can be employed to stop liquid flow through a tube 110, to allow liquid flow through a tube 110 or to control the flow rate of liquid through a tube 110.

Figure 17B:
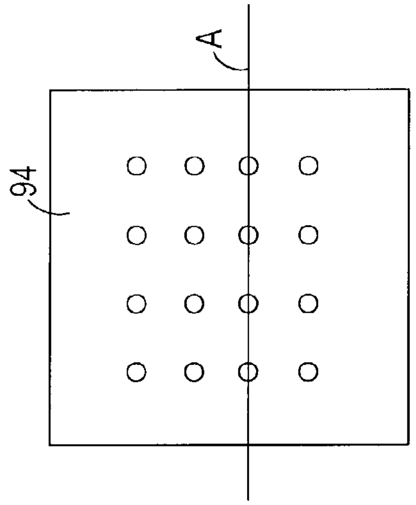
FIG. 17B is a bottomview of the interface system illustrated in FIG. 17A.
Figure 17A:
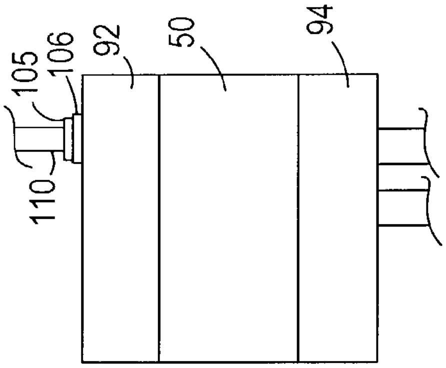
FIG. 17A is a sideview of a liquid transport structure positioned between the first interface member and the second interface member of an interface system configured for in conjunction with sealing mechanisms for sealing inlet channels on a liquid transport structure.
Figure 17C:
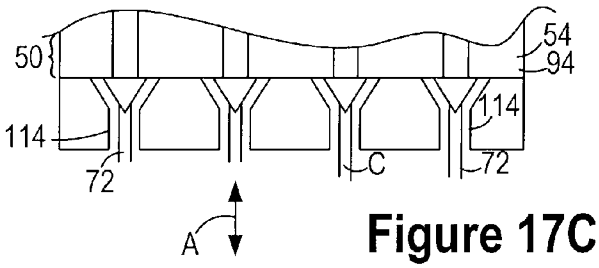
FIG. 17C is a cross section of the interface system taken along the line labeled A in FIG. 17B.

FIG. 17A through FIG. 17C illustrate an interface system 90 for use with a liquid transport structure 50 constructed in accordance with FIG. 10A through FIG. 10C. FIG. 17A is a sideview of a liquid transport structure 50 positioned between the first interface member 92 and the second interface member 94 of an interface system 90. FIG. 17B is a bottomview of the interface system 90 illustrated in FIG. 17A. FIG. 17C is a cross section of the interface system 90 taken along the line labeled A in FIG. 17B.

The interface system 90 can be employed with a liquid transport structure 50 constructed according to FIG. 10C. Accordingly, the first member 52 of the liquid transport structure 50 can include a single vent channel 68. Hence, the first interface member 92 is illustrated with a single connector 104 for providing liquid communication between a tube 110 and the vent channel 68.

The second interface member 94 includes a plurality of guide lumens 114. The guide lumens 114 are positioned such that each of the guide lumens 114 is aligned with an inlet channel 66 when the second interface member 94 is positioned adjacent to the liquid transport structure 50. The sealing mechanisms can be moved within the guide lumens 114 as illustrate by the arrow labeled A. Each guide lumen 114 guides the movement of the sealing mechanism relative to the liquid transport structure 50. For instance, when a sealing mechanism is employed to seal an inlet channel 66, the guide lumen 114 guides the movement of the sealing mechanism into contact with the liquid transport structure 50.

The interface system 90 of FIG. 17A through FIG. 17C can be employed with a liquid transport structure according to FIG. 11A through FIG. 11G. For instance, the liquid transport structure can include one or more diaphragms 74 positioned as shown in FIG. 11A through FIG. 11G. The guide lumens 114 can be configured to guide the movements of the implements 76 into contacted with the diaphragms 74.

In some instances an interface member will not include any lumens. For instance, when a member of the liquid transport structure 50 does not include any channels, the adjacent interface member need not include any lumens. As a result, the adjacent interface member can be a slab.

Figure 18A:
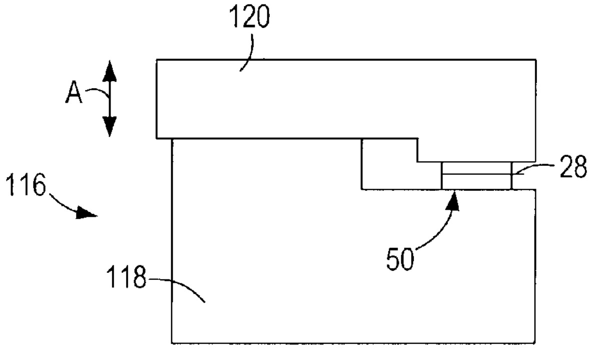
FIG. 18A is a sideview of assay equipment for use with a liquid transport structure that serves as a cartridge that can be incorporated into and removed from the assay equipment.
Figure 18B:
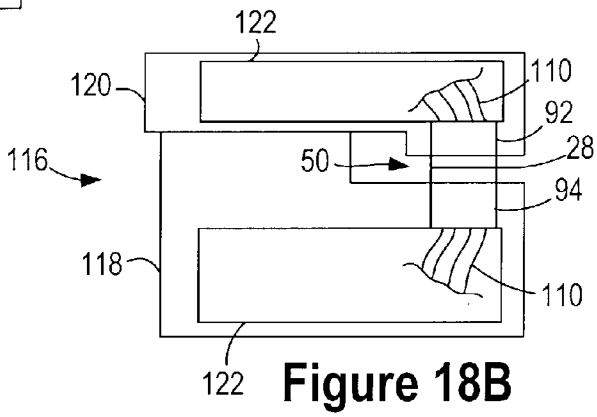
FIG. 18B is a cross sectional view of the assay equipment shown in FIG. 18A.

In some instances, the liquid transport structure 50 serves as a cartridge that can be easily incorporated into and removed from assay equipment including equipment such as the pumps, vacuums, valves and/or electronics discussed above. FIG. 18A is a sideview of assay equipment for use with a liquid transport structure 50 that serves as a cartridge. FIG. 18B is a cross sectional view of the assay equipment shown in FIG. 18A.

The illustrated assay equipment includes a frame 116 with a base 118 and an upper body 120. The upper body 120 can be moved relative to the base 118 as illustrated by the arrow labeled A. The base 118 holds the second interface member 94 while the upper body 120 holds the first interface member 92. The liquid transport structure 50 is configured to be coupled with the frame 116 during operation of the assay system and can be removed from the frame 116. The liquid transport structure 50 can be coupled with the frame 116 by positioning the liquid transport structure 50 on the second interface member 94 and lowering the upper body 120 toward the base 118 until the liquid transport structure 50 is clamped between the first interface member 92 and the second interface member 94 as shown in FIG. 18A. The liquid transport structure 50 can be removed from the frame 116 by moving the upper body 120 away from the base 118 and removing the liquid transport structure 50 from the second interface member 94.

When the liquid transport structure 50 is coupled with the frame 116, the sensors 10 can be in electrical communication with electronics (not shown) for operating the sensors 10. This electrical communication can be achieved by inserting the pads 34 of the chip into a port that provides electrical communication between the sensors 10 and the electronics before or after the liquid transport structure 50 is coupled with the assay equipment.

The upper body 120 of the frame 116 and/or the lower body of the frame 116 can include a chamber 122 where various equipment is positioned. For instance, a chamber 122 can hold the pumps, vacuums, valves and/or electronics discussed above. Alternatively, the pumps, vacuums, valves and/or electronics can be located outside of the frame 116. The electronics can operate the pumps, vacuums and valves so as to create the desired pressure in the channels of the liquid transport structure 50. Accordingly, the electronics can control the transport of the liquid from a reservoir into the assay chamber.

Figure 18C:
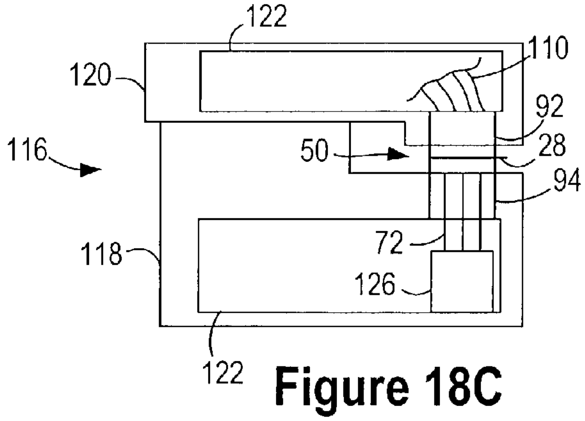
FIG. 18C is a cross section of assay equipment that is suitable for use with a liquid transport structure constructed according to FIG. 10A through FIG. 10C.

FIG. 18C is a cross section of assay equipment that is suitable for use with a liquid transport structure 50 constructed according to FIG. 10A through FIG. 10C. The base 118 holds a second interface member 94 constructed according to FIG. 17C. The base 118 also holds a plurality of sealing mechanisms extending through the second interface member 94. Each sealing mechanism 72 is coupled with an actuator 126 configured to independently move each sealing mechanism 72 through the associated guide lumen 114. A suitable actuator 126 includes, but is not limited to, a stepped motor, a linear actuator or a bubble actuator. Electronics (not shown) can control the actuators. For instance, the electronics can engage a particular actuator to move a sealing mechanism through the associated guide lumen 114 and unseal an inlet channel 66. Accordingly, the electronics can control the transport of the liquid from the liquid transport structure 50 onto a sensor 10.

The sealing mechanisms shown in FIG. 18C can be replaced with the instruments discussed in FIG. 11A through FIG. 11G. Accordingly, the actuator 126 can be employed to move the instrument 76 into contact with a diaphragm on the liquid transport structure.

Although the first interface member and the second interface member are shown as being independent of the frame, the first interface member and/or the second interface member can be integrated into the frame.

Although the liquid transport structure is illustrated above as being constructed from a first member and a second member, the first member and the second member can be formed into a single piece. As a result, the liquid transport structure can have a one-piece construction or a multi-piece construction.

Although the liquid transport structure is disclosed in the context of a particular sensor embodiment, the liquid transport structure can be employed other sensor types and constructions. For instance, the liquid transport structure can be employed with sensors other than electrochemical sensors. Further, the sensor need not be limited to detection of biological agents and can be a sensor for the detection of other agents such as chemicals and particulates, electrolytes and molecules.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

What is claimed is:

1. A liquid transport structure for use with an assay, comprising:

a plurality of sensors positioned on a sensor support and a plurality of electrical contact pads positioned on the sensor support, each sensor including a plurality of electrodes, the electrodes included in each one of the sensors including a working electrode, a counter electrode, and a reference electrode, each of the electrodes being in electrical communication with a different one of the contact pads;

a first member including a recess extending part way into a first side of a first member substrate, the first member substrate being a single layer of material;

a reservoir within the first member, the reservoir being partially defined by a recess extending part way into a second side of the first member substrate, the second side of the first member substrate being opposite the first side of the first member substrate;

an inlet channel for transporting a liquid from outside of the liquid transport structure into the reservoir; and an outlet channel for transporting a liquid held in the reservoir to the recess extending part way into the first side of the first member substrate;

a second member comprising a second member substrate; and the first member and the second member being independent of the sensor support and being configured to be coupled with the sensor support such that the sensor support is between the first member and the second member and such that the contact pads are not covered by either the first member or the second member, the first member and the second member being configured to be coupled with the sensor support such that one of the sensors is positioned in a chamber that is at least partially defined by the recess extending part way into the first side of the substrate and such that a waste channel that extends from the chamber through the sensor support and through the second member to outside of the liquid transport structure is at least partially defined by the sensor support and the second member substrate.

2. The apparatus of claim 1, wherein the reservoir is one of a plurality of reservoirs within the first member; and the outlet channel is one of a plurality of outlet channels included in the first member, each of the outlet channels being configured to transport a liquid from one of the reservoirs to one of the sensors such that each of outlet channels is configured to transport the liquid to a different one of the sensors.

3. The apparatus of claim 1, wherein the first member and the second member are configured to be coupled with the sensor support such that a plurality of the sensors are positioned in the chamber.

4. The apparatus of claim 1, wherein the inlet channel extends from an external side of the first member to the reservoir.

5. The apparatus of claim 1, wherein the outlet channel includes an obstruction positioned so as to obstruct the outlet channel.

6. The apparatus of claim 5, wherein the obstruction includes one or more openings through which the liquid in the reservoir can flow.

7. The apparatus of claim 1, wherein the liquid transport structure is substantially block shaped.

8. The apparatus of claim 1, wherein the liquid transport structure has a volume less than 16 cubic inches.

9. The apparatus of claim 1, wherein the liquid transport structure is coupled with an interface system, the interface system providing liquid communication between the reservoir and a tube.

10. The apparatus of claim 1, wherein at least one channel extends from an external side of the first member to a lateral side of the recess extending part way into the first side of the first member substrate.

11. The apparatus of claim 10, wherein the at least one channel includes a nozzle.

12. The apparatus of claim 11, wherein a diaphragm obstructs the inlet channel.

13. The apparatus of claim 12, wherein the diaphragm includes one or more openings through which a fluid can flow.

14. The apparatus of claim 1, wherein the first member substrate is positioned over the sensor and the second member substrate is positioned under the sensor.

15. The apparatus of claim 1, wherein each of the electrodes are positioned on an electrode support bonded to the sensor support.

16. The apparatus of claim 15, wherein the electrode support includes a first support region spaced apart from a second support region with air being located between the first support region and the second support region, one or more of the electrodes positioned on the first support region and one or more of the electrodes positioned on the second support region.

17. The apparatus of claim 15, wherein the electrode support is positioned between the electrodes and the sensor support.

18. The apparatus of claim 1, wherein a sealing medium is positioned over the inlet channel.

19. The apparatus of claim 1, wherein the first member at least partially covers a top of the reservoir.

20. The apparatus of claim 19, wherein a portion of the first member covering the top of the reservoir is impermeable to liquids.

21. The apparatus of claim 1, wherein an electrode support includes a first support region spaced apart from a second support region such that air is located between the first support region and the second support region and one or more of the electrodes are positioned on the first support region and one or more of the electrodes are positioned on the second support region.

22. The apparatus of claim 1, wherein the outlet channel extends through the first member substrate from the reservoir to the recess extending part way into the first side of the first member substrate.

23. The apparatus of claim 1, further comprising:

a cover positioned on the first member substrate and defining a portion of the reservoir, the inlet channel extending through the cover.

24. The apparatus of claim 1, wherein at least a portion of the reservoir is positioned over the recess extending part way into the first side of the first member substrate.

25. The apparatus of claim 1, wherein the first member includes a deformable diaphragm obstructing the inlet channel when the diaphragm is not deformed.

26. The apparatus of claim 1, wherein the contact pads are positioned along an edge of the sensor support.

27. The apparatus of claim 1, wherein the sensor support includes a sensor support substrate.

28. The apparatus of claim 1, wherein each sensor includes the working electrode positioned between the reference electrode and the counter electrode with the reference electrode spaced apart from the working electrode and the counter electrode spaced apart from the counter electrode.

29. The apparatus of claim 1, wherein the chamber is one of a plurality of chambers that are each partially defined by a different recess extending part way into the first side of the first member substrate, and the first member and the second member are configured to be coupled with the sensor support such that each of the sensors is positioned in a different one of the chambers.

* * * * *